United States Patent
Regensburger

(10) Patent No.: US 11,602,398 B2
(45) Date of Patent: Mar. 14, 2023

(54) METHOD AND SYSTEM FOR THE NAVIGATIONAL SUPPORT OF A PERSON FOR NAVIGATION RELATIVE TO A RESECTATE, COMPUTER PROGRAM AND ELECTRONICALLY READABLE DATA MEDIUM

(71) Applicant: Siemens Healthcare GmbH, Erlangen (DE)

(72) Inventor: Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 355 days.

(21) Appl. No.: 16/894,880

(22) Filed: Jun. 7, 2020

(65) Prior Publication Data
US 2020/0383733 A1   Dec. 10, 2020

(30) Foreign Application Priority Data
Jun. 7, 2019   (DE) .......................... 102019208355.2

(51) Int. Cl.
*G06K 9/00*   (2022.01)
*A61B 34/20*   (2016.01)
(Continued)

(52) U.S. Cl.
CPC .............. *A61B 34/20* (2016.02); *A61B 90/20* (2016.02); *A61B 10/00* (2013.01);
(Continued)

(58) Field of Classification Search
CPC ......... A61B 34/20; A61B 90/20; A61B 10/00; A61B 2017/320064; A61B 2034/2065;
(Continued)

(56) References Cited

U.S. PATENT DOCUMENTS 9,317,634 B2 *   4/2016   Davison ............... A61B 17/152
9,833,254 B1 *   12/2017   Barral .................... A61B 90/30
(Continued)

FOREIGN PATENT DOCUMENTS

DE   102012223651 A1   6/2014
DE   102014103044 A1   9/2015
(Continued)

OTHER PUBLICATIONS

German Office Action for German Application No. 10 2019 208 355.2 dated Mar. 10, 2020.

*Primary Examiner* — Shervin K Nakhjavan
(74) *Attorney, Agent, or Firm* — Lempia Summerfield Katz LLC

(57) ABSTRACT

A method for navigational support of a person performing a resection on a patient following extraction of a resectate includes recording a first surface data set of the resectate using an ex vivo scan appliance, and determining a second surface data set of the extraction region using a recording instrument. The second surface data set covers at least one part of the remaining tissue surface of the extraction region of the resectate in the patient. The method also includes registering the first surface data set of the resectate with the second surface data set of the extraction region based on corresponding surface features of the resectate and the remaining tissue surface in the extraction region, and performing at least one support measure that supports the navigation in the extraction region relative to the resectate, using the registration.

31 Claims, 8 Drawing Sheets

(51) Int. Cl.
*A61B 90/20* (2016.01)
*A61B 90/00* (2016.01)
*G16H 30/20* (2018.01)
*A61B 10/00* (2006.01)
*A61B 17/32* (2006.01)

(52) U.S. Cl.
CPC .............. *A61B 2017/320064* (2013.01); *A61B 2034/2065* (2016.02); *A61B 2090/364* (2016.02); *A61B 2090/3735* (2016.02); *G16H 30/20* (2018.01)

(58) Field of Classification Search
CPC ...... A61B 2090/364; A61B 2090/3735; A61B 90/36; A61B 2034/105; A61B 2090/365; A61B 2090/371; A61B 2090/502; A61B 17/320016; A61B 2034/2051; A61B 2034/2055; A61B 2090/372; A61B 2090/376; A61B 2090/3941; A61B 2090/395; A61B 34/10; A61B 10/0233; A61B 90/361; A61B 2034/207; G16H 30/20; G16H 20/40; G16H 40/67; G16H 50/20; G16H 50/50
See application file for complete search history.

(56) References Cited

U.S. PATENT DOCUMENTS

| | | | |
|---|---|---|---|
| 10,292,769 B1* | 5/2019 | Yu | A61B 34/10 |
| 2015/0250387 A1 | 9/2015 | Hauger | |
| 2015/0327767 A1* | 11/2015 | Hellmich | A61B 5/742 |
| | | | 600/407 |
| 2016/0067007 A1* | 3/2016 | Piron | G16H 40/20 |
| | | | 705/3 |
| 2016/0135776 A1* | 5/2016 | Chandler, Jr. | G06T 7/33 |
| | | | 600/411 |
| 2016/0143693 A1* | 5/2016 | Yilmaz | A61B 6/12 |
| | | | 606/130 |
| 2017/0086675 A1* | 3/2017 | Li | A61B 5/0086 |
| 2017/0105601 A1 | 4/2017 | Pheiffer | |
| 2017/0143430 A1* | 5/2017 | Miga | A61B 90/39 |
| 2017/0358083 A1* | 12/2017 | Piron | A61B 34/30 |
| 2019/0287246 A1 | 9/2019 | Pfister | |
| 2019/0365475 A1* | 12/2019 | Krishnaswamy | A61B 34/10 |
| 2020/0197100 A1* | 6/2020 | Leung | A61B 34/20 |
| 2020/0383729 A1* | 12/2020 | Amanatullah | A61B 17/154 |
| 2020/0405398 A1* | 12/2020 | Amanatullah | G09B 23/28 |

FOREIGN PATENT DOCUMENTS

| | | |
|---|---|---|
| EP | 3540632 A1 | 9/2019 |
| WO | 2016109878 A1 | 7/2016 |

\* cited by examiner

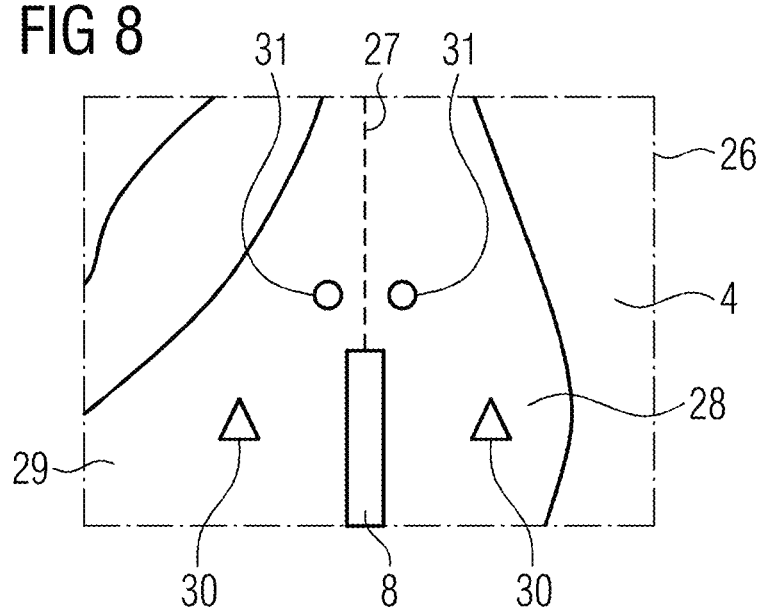
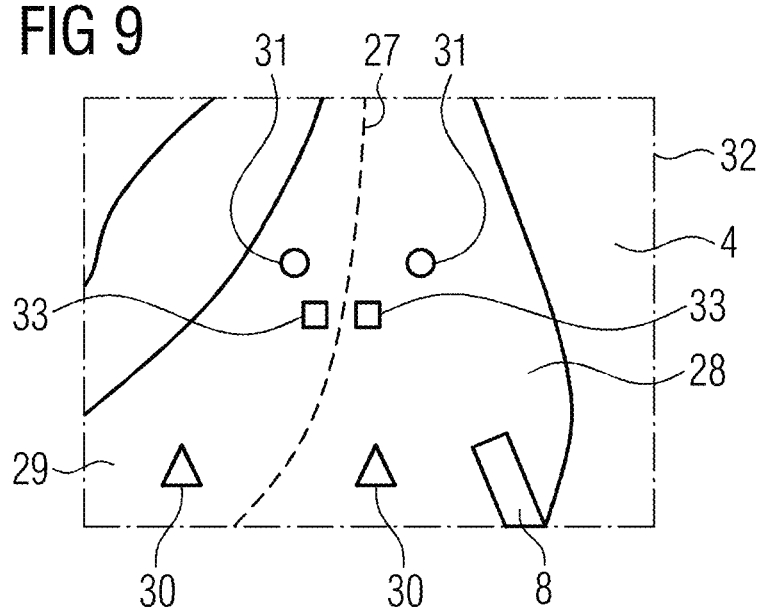

METHOD AND SYSTEM FOR THE NAVIGATIONAL SUPPORT OF A PERSON FOR NAVIGATION RELATIVE TO A RESECTATE, COMPUTER PROGRAM AND ELECTRONICALLY READABLE DATA MEDIUM

This application claims the benefit of German Patent Application No. DE 10 2019 208 355.2, filed on Jun. 7, 2019, which is hereby incorporated by reference in its entirety.

BACKGROUND

The present embodiments relate to navigational support of a person performing a resection on a patient following extraction of a resectate, for navigation relative to the resectate in the extraction region.

One way of treating the presence of malignant tissue such as a tumor within a patient is the removal of the malignant tissue. This procedure is also referred to as resection; the portion of tissue, which may contain all of the malignant tissue, is referred to as a resectate. The objective in this case is an R0 resection, providing that no more malignant tissue should be evident in the resection edge or that a defined minimum distance to the malignant tissue is satisfied. For example, following a tumor resection, a surgeon would like to know as quickly and meaningfully as possible whether the resection was successful in oncological terms, and therefore, that no remaining tumor tissue should be present in the patient body. In the event that an R0 resection is not achieved, and if the information is rapidly available, a follow-up resection may be performed quickly, and additional tissue may be removed.

In this context, it is customary, for example, to perform a fast slice diagnosis of the resectate in pathology. In this case, tissue slices are prepared, and a test establishes whether the distances of malignant tissue from the edge of the resectate are satisfactory. After approximately 10 to 15 minutes, the relevant findings may be reported back to the operating theatre (e.g., by telephone).

In order to improve the situation in this regard, digital histology devices (also referred to as ex vivo scan appliances) have been provided for the operating theatre. In this case, the resectate that is removed from a patient (e.g., following a tumor operation) may be scanned at its surface in order to give an indication concerning the presence of malignant tissue at the surface of the resectate. A fast slice diagnosis may still be performed by a pathologist after this. However, the findings of the ex vivo scan appliance are available immediately in the operating theatre. The doctor may therefore look at the results of the digital histology device and estimate approximately where a follow-up resection will probably be required. However, the problem arises here that this only corresponds to a rough estimate, and it is possible that a follow-up resection will be incorrect and/or far too large.

Also provided are digital biopsy tools that allow point-based recordings in the operating field. Here, a small sector of the surface resulting from extraction of the resectate (e.g., in the region of a few square millimeters) is scanned using optical methods (e.g., microscopy and/or optical coherence tomography).

Such a digital biopsy tool is disclosed in DE 10 2014 103 044 A1, for example. There, a group of devices includes at least an endomicroscope for capturing cellularly resolved image data from an operating field. Provision may also be made for an imaging apparatus, specifically an operation microscope for recording overview image data from the operating field.

A problem relating to such digital biopsy tools is that sectors may only be scanned at specific points, and therefore, a large-area scan is not practicable due to the large amount of time required. A large-area scan may be an area of at least 1 $cm^2$ in this case.

US 2017/0105601 A1 relates to a method and a system for calculating a volume of resectioned tissue (e.g., a resectate) from a series of intraoperative images. The 2-dimensional or 2.5-dimensional intraoperative images recorded using, for example, a laparoscope are recorded from different angles relative to the resectate. A resectioned tissue surface is segmented in each of the intraoperative images. The segmented tissue surfaces are combined, and a three-dimensional point cloud representation of the surface of the resectate is thus obtained. This may then be used to determine the volume.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a person performing a resection is provided with an improved way for assigning features of a resectate to extraction region.

One embodiment of a method for navigational support of a person performing a resection on a patient following extraction of a resectate, for navigation relative to the resectate in the extraction region, includes recording a first surface data set of the resectate using an ex vivo scan appliance, and determining a second surface data set of the extraction region using a recording instrument. The second surface data set covers at least one part of the surface of the extraction region of the resectate in the patient. The method also includes registering the first surface data set of the resectate with the second surface data set of the extraction region based on corresponding surface features of the resectate and the surface of the remaining tissue in the extraction region, and performing at least one support measure that supports the navigation in the extraction region relative to the resectate, using the registration.

The present embodiments therefore provide establishing a surface-based correspondence between locations on the resectate and locations on the remaining tissue surface in the extraction region resulting from the extraction of the resectate in the body of the patient, such that if a relevant indicative feature is known in a position on the surface of the resectate, the support measure (e.g., by presenting a depiction) is suitable for the purpose of guiding the person performing the resection to the corresponding location on the surface in the extraction region or to allow this corresponding location to be found more quickly. Microscopic and macroscopic cell structures and/or tissue structures form identifiable surface features in surface data or in image data generally. Strong similarities of these features at the resectate and at the surface region previously connected thereto in the extraction region may exist, since the features originally formed a continuous or almost continuous structure before the resection was performed and were only cut apart during the performance of the resection. Alternatively, as described in greater detail below, if the interrelationship between clearly identifiable surface features is harder to recognize, the correspondence may also be established by observation during the resection process. Examples of similarities that may be found include patterns in the arrangement of cells, tissue boundary layers, blood vessels, tissue densities, and cell types, as well as possibly the infiltration pattern of tumor cells.

Corresponding features therefore indicate corresponding locations on the respective surfaces. In this case, locations on the surface of the resectate correspond to locations on the surface of the extraction region resulting from the removal of the resectate if the locations were directly or almost directly continuous before the resection. In other words, the registration methods described are used to assign locations on the surface remaining in the patient and resulting from the resection, to those locations on the surface of the resectate to which the locations were previously closest. A location (e.g., an indicative feature) on the surface of the resectate is designated as $a_R$. The corresponding location on the surface in the extraction region resulting from the resection is designated as by. In this case, $a_R$ may be defined either two-dimensionally on a suitable coordinate system of the tissue surface of the resectate, or three-dimensionally in a 3D coordinate system of the resectate or surface thereof; for $b_V$, this applies correspondingly to a coordinate system of the remaining tissue surface or the remaining tissue volume, where use may be made of a patient-related coordinate system or at least a coordinate system that is registered with such a patient-related coordinate system. The patient-related coordinate system is used, for example, by a navigation system that may track instruments and/or devices, for example. For example, the correspondence of the locations may be mathematically defined as follows. $B_V$ designates the three-dimensional location in the continuous tissue before the resection, at which the cells/tissue element at the location by of the remaining tissue after the resection were originally situated. $A_R$ correspondingly designates the three-dimensional location in the continuous tissue before the resection, at which the cells/tissue element at the location $a_R$ of the resectate were originally situated. As "corresponding to $a_R$" is designated as location by, from the set {b} of all locations of the remaining tissue surface resulting from the resection, which, as location By in the original three-dimensional continuous tissue volume, had the minimal distance to $A_R$.

The registration result therefore allows locations on the surface of the resectate to be assigned corresponding locations on the surface in the extraction region in the patient. It is thereby possible to establish an association between digital histology and intraoperative navigation/imaging. The person performing the resection is supported in the rapid and targeted correction of, for example, incomplete resections. The results of the digital histology may be transferred directly into the operating field, thereby allowing the immediate correction of an error in the resection.

The recording instrument may be tracked in a patient-related coordinate system by a navigation system, where the second surface data set is also recorded, determined, or present in the patient-related coordinate system. In this case, the support measure may include, for example, a depiction of the position of at least one indicative feature of the resectate relative to the recording instrument and/or to a further instrument that is tracked by the navigation system in the patient-related coordinate system and/or to the surface of the extraction region. A navigation system that works in a patient-related coordinate system may therefore be used in an advantageous manner. If the second surface data set is now available in the same coordinate system (e.g., because the recording instrument is tracked by the navigation system in any case) or may at least be converted into the patient-related coordinate system, it is possible, based on the registration result for evaluation results (e.g., indicative features) for the first surface data set (e.g., location-related information about the implant) to be localized in the patient-related coordinate system by virtue of the registration result, and consequently deployed there for support measures, for example. For example, a depiction relative to other information available in the patient-related coordinate system may therefore be provided (e.g., a relative position of indicative feature and recording instrument and/or other instruments and tools in use). In addition to support measures based on depiction, which make the person performing the resection intuitively conscious of the position of indicative features of the resectate in the patient-related coordinate system, further support measures may also be provided in the context of the present embodiments (e.g., navigation-type target guidance outputs and the like). For example, support measures based on depiction may be supported by further output measures as support measures (e.g., in the form of acoustic navigation in which the frequency of the succession of tones increases as an instrument/tool comes closer to an indicative feature, etc.).

As mentioned above, the indicative feature may be determined, for example, by evaluating the first surface data set and/or a further image data set of the resectate that is registered with the first surface data set. The further image data set of the resectate may likewise be recorded using the ex vivo scan appliance. For example, an ex vivo scan appliance may be developed to record the resectate using different modalities (e.g., by a camera and/or a microscope and/or optical coherence tomography and/or fluorescence imaging). The modality that best corresponds to the modality of the second surface data set is selected for the first surface data set. As a result of using the same ex vivo scan appliance, any further image data sets of the resectate are then automatically registered with the first surface data set of the resectate.

One or more of the at least one indicative feature may also be provided by the complete first surface data set and/or the complete further image data set, optionally also in annotated form. For example, a possible support measure may therefore be to present a depiction of the optionally pre-evaluated and/or annotated first surface data set and/or further image data set together with an instrument/tool or a corresponding marking on a display appliance.

In this context, provision may be made for one or more of the at least one indicative feature to describe the presence of a malignant change in the resectate in a defined proximity to the surface of the resectate. The presence is determined by at least partially automatic evaluation of the first surface data set and/or a further image data set of the resectate that is registered with the first surface data set. In the case of a tumor resection, tumor cells lying at or extremely close to the surface (e.g., at less than a safety distance describing the defined proximity) and/or locations exhibiting infiltration patterns may be used as the indicative feature in this way. Since the resection usually serves to extract malignant tissue, such indicative features therefore clearly signal the points at which a follow-up resection is required or advisable. Using corresponding support measures that make use of the indicative feature, these regions may be found in a way that is far easier and more intuitive since, by virtue of the registration result, locations on the resectate may be converted into locations that are described within the patient-related coordinate system and vice versa.

In order to depict the relative position, use may appropriately be made of an augmented reality appliance (e.g., an augmented reality headset) and/or a display appliance for the purpose of presenting the first surface data set and/or the second surface data set. The instrument and/or the further instrument and/or a marking displaying a respective relative position is incorporated in the first surface data set and/or the second surface data set, and/or for the purpose of presenting a current image of the recording instrument and/or one or more of the at least one further instrument (e.g., a laparoscope). The at least one indicative feature from the first surface data set is incorporated in the image. In this case, it may be appropriate to depict the first surface data set and/or the second surface data set as a surface map. This is possible both two-dimensionally and three-dimensionally with a corresponding recording modality. In the context of the present embodiments, regions in which the malignant change described by one or more of the at least one indicative feature is present may be displayed in a positionally accurate manner in the extraction region and/or in the current image of the extraction region when an augmented reality appliance (AR appliance) is used.

In other words, the present embodiments allow the widest possible range of visualization variants as support measures in order to be able to provide the support with respect to indicative features at the resectate. It is therefore possible, for example, to display a two-dimensional or three-dimensional surface map (e.g., a tissue map and/or other representation of the resectate; in the form of the (annotated) first surface data set and/or further image data set, including colored regions showing malignant tissue change, such as tumor cells). An instrument (e.g., the recording instrument and/or a digital biopsy tool and/or navigated intervention instrument) may be incorporated as virtually moving over the map based on the registration result. This provides that while the instrument in real space is situated at a location or in the proximity of a location at the surface of the remaining tissue in the extraction region, the instrument is virtually incorporated at the corresponding location on the surface of the resectate, or the corresponding location/region is otherwise marked. Both two-dimensional and three-dimensional depiction variants may be provided in this case, depending on the format of the surface data sets and further information.

According to a further visualization variant, for example, regions with malignant changes (e.g., with tumor cells) are again used as an indicative feature, but the surface regions corresponding to regions with tumor cells on the surface of the resectate are depicted on the remaining surface of the remaining tissue, resulting from extraction of the resectate, as augmented reality and/or on a virtual two-dimensional or three-dimensional surface model or a surface map (e.g., including incorporation of the navigated instruments).

As mentioned above, provision may be made for the first surface data set and/or the second surface data set and/or the further image data set to be recorded using an optical imaging modality (e.g., a camera and/or optical coherence tomography and/or fluorescence imaging and/or confocal microscopy and/or laser microscopy). In this case, it is possible, for example, for the first surface data set and the second surface data set to be recorded using different modalities. For example, the surface of the resectate may be scanned over a large area by the ex vivo scan appliance using optical coherence tomography, while the surface of the remaining tissue resulting from the extraction of the resectate in the extraction region is recorded in a point-based manner (e.g., in very small sectors) using optical confocal microscopy. According to a further embodiment, the surface of the resectate is recorded over a large area using high-resolution optical microscopy, while the surface of the remaining tissue is recorded using a low-resolution laparoscope or operation microscope.

In one embodiment, a plurality of different modalities in each case for first and/or second surface data sets may be used. For example, the surface of the resectate may be surveyed using two modalities that are registered with each other (e.g., both scan laser microscopy and an image from an overview camera that is integrated in the microscope). In such a case, an approximate registration may be performed, for example, based on the first surface data set of the overview camera, or a plurality of candidates may be specified for an approximate registration that may then be fine-tuned or validated in or using microscopic methods. Possibilities for nonetheless combining such different modalities in the context of a registration process are described in greater detail below.

In an embodiment, as the recording instrument, a digital biopsy tool that surveys the tissue surface in the extraction region in a sector-based manner (e.g., in a sector of 0.01 to 10 $mm^2$ in size) may be used. The corresponding sector is localized on the surface of the resectate in the context of the registration. In this case, in addition to the ex vivo scan appliance that allows large-area surface recordings of the resectate, a digital biopsy tool is deployed for "point-based" recordings (e.g., microscopically and/or by optical coherence tomography) in the operating field. The digital biopsy tool is ideally tracked by the navigation system, as described above. The navigation system in general may be configured as an optical and/or electromagnetic navigation system, for example, as known in principle from the prior art, and need not be described in greater detail here.

Tracking of the digital biopsy tool by a or the navigation system may be applicable if a plurality of sectors are to be recorded. It is therefore appropriate in general for the second surface data set to include measurements for a plurality of sectors. The position and orientation (e.g., pose) of the digital biopsy tool may be determined via the navigation system, and consequently, the sectors are known in the corresponding relative arrangement. With regard to the registration, for example, the registration may be effected for one sector first; it is then checked whether this is also valid for the remaining sectors. Other registration approaches may also be selected. If the second surface data set includes a plurality of sectors, these may be selected to be largely evenly distributed, so that digital measurement samples are ultimately available for different regions of the remaining tissue surface and therefore for the resectate likewise.

In a development, the first surface data set may be evaluated to result in at least one region with surface features that are identifiable in the surface data of the digital biopsy tool being determined and displayed to the person in relation to the resectate. It is therefore already possible, by a pre-evaluation process of the first surface data set, to deduce which region (e.g., extensive region) contains many surface features that are particularly suitable with regard to registration, so that the person performing the resection may be specifically directed to corresponding regions on the resectate. If the regions are extensive in this context, the person is able with reference to the resectate to assign at least approximately where the digital biopsy tool is to be positioned in the extraction region. Further support for the person performing the intervention is provided in this way.

In an advantageous development, a quality level may be determined in the context of the registration, describing the reliability of the registration result. A recording of a further sector is requested if the quality level fails to meet a threshold value. Alternatively or additionally, at least one verification measurement may be performed using the digital biopsy tool in order to check information given by the support measure (e.g., for checking the presence of a malignant change at a current position of the digital biopsy tool). An iterative procedure may therefore take place, providing that it is possible (e.g., starting from a specific number of surveyed sectors, such as one to five sectors), for example, to check after each registration process whether a desired registration quality is achieved. Quality levels that describe the registration quality and hence the reliability of the registration are already provided in the prior art and may also be deployed in the context of the present embodiments. Such quality levels are frequently included in algorithms or partial algorithms that are already known. If the quality of the registration is not good enough (e.g., if the quality level fails to meet a threshold value for the quality level), further measurements using the digital biopsy tool may be requested in order thereby progressively to increase the registration quality.

A particularly advantageous check may also be performed by the digital biopsy tool. If the support measures have guided the person performing the resection, for example, to a point in the extraction region where a continuation of the malignant change is feared at the surface, or where a correspondence to a relevant surface feature (e.g., an indicative feature) of the resectate should exist, the support measures allow the digital biopsy tool that is tracked by the navigation system to be guided to these corresponding locations on the remaining tissue surface, whereupon it is possible to verify using measurement by the digital biopsy tool whether the displayed correspondence of the locations and hence of the surface features was determined correctly in the registration process. From the recordings of the digital biopsy tool, the person may also directly assess whether malignant changes are also present on the remaining tissue side (e.g., an infiltration of tumor cells). Such a repeated measurement may also be used to refine the registration of at least one sector at these locations based on the additional data.

In the case of malignant changes, for example, it is optionally possible (e.g., outside the method described here) to perform a follow-up resection in order to remove malignant tissue changes that may be present.

In the context of the present embodiments, it is additionally or alternatively conceivable for the first surface data set and/or the second surface data set to be assembled from partial data sets (e.g., of a stereo camera) that were recorded from different directions of view relative to the resectate or the extraction region. Using, for example, the method described in US 2017/0105601 A1 cited in the introduction, with regard to the resectate, it is possible, for example, by rotating the resectate in front of a stereo camera to generate three-dimensional surface models of the resectate and/or of the surface resulting from extraction of the resectate in the extraction region. For example, provision may therefore be made for initially determining a surface model that describes the surface contour (e.g., as a polygon model) from the partial data sets. The image data of the partial data sets is assigned to the model as texture. This provides that the camera image data constitutes a texture for the surface (e.g., the polygonal surface) that is defined by the surface model.

If the first surface data set, which is assembled from partial data sets recorded from different directions of view relative to the resectate, is not recorded using the ex vivo scan appliance but, for example, using a laparoscope and/or other recording instrument, provision may be made for this first surface data set to be registered with a second first surface data set from the ex vivo scan appliance. This may easily be achieved using current registration methods since the same surface is recorded. For example, using image analysis, it is possible, using suitable analysis algorithms and possibly interpolation/smoothing, to effect a registration of the large-area scan results of the ex vivo scan appliance with the 3D surface model of the resectate (e.g., based on macroscopic tissue structures that are contained in both the scan data of the ex vivo scan appliance and in the image data of the corresponding stereo camera of the recording instrument, such as a laparoscope). A further possibility is the use of markers on the resectate in order to achieve the registration of such multiple first surface data sets, of which one was not recorded using the ex vivo scan appliance. The ex vivo scan appliance that is already available may, however, simply be used.

According to a development, when determining a second surface data set showing the whole surface of the extraction region formed by the resection, and using a digital biopsy tool that surveys the tissue surface in the extraction region in a sector-based manner, a sector surveyed by the digital biopsy tool is registered on the second surface data set (e.g., with the aid of the first surface data set that is registered with the second surface data set). This provides that the measurement points (e.g., sectors) of the digital biopsy tool, which is tracked, for example, are registered directly with the 3D surface model of the remaining tissue surface. The detection of correspondences may be assisted by the geometrical correlation of the three-dimensional surface models of resectate and remaining tissue surface.

In an embodiment, following the recording of the first surface data set, provision may be made for this to be first evaluated for the presence of a malignant change in the resectate in a defined proximity to the surface of the resectate. If no malignant changes are identified in the resectate in a defined proximity to the surface of the resectate, the method is terminated, and therefore, no recording is made of the second surface data set, and correspondingly, no registration takes place. If no malignant changes exist at the surface itself or up to a normally defined safety distance, this indicates an R0 resection, and therefore, the resection may be considered as complete. If, however, relevant malignant changes are still identified in the surface region of the resectate, the person performing the resection may be shown that an R0 resection has not been achieved and that a follow-up resection may be necessary. The person performing the resection may then use, for example, the recording instrument or corresponding recorded image data in a selective manner to obtain the second surface data set.

In the context of the present embodiments, there are two fundamental approaches for achieving a registration of the first and second surface data sets. Both approaches, which may be applied in combination, are presented in greater detail below.

In this case, the first approach is founded on the basic assumption that there are similarities in the respective surface imaging between the corresponding surface locations and hence surface features of resectate and extraction region (e.g., remaining tissue). The similarities allow a pattern-based or image-based registration. Examples of such tissue patterns or tissue properties, which allow the assignment between surface features of resectate and remaining tissues based on similarities, include the cell structure, cell types, the arrangement of cells, the fiber structure of the tissue, the vascular structure of the tissue, the spectral reflectivity (color) of the tissue, the distribution of a fluorescent dye in the tissue, the distribution of malignant changes (e.g., tumor cells) on the visible tissue surface, and application patterns of an intervention instrument.

In an appropriate specific embodiment of the registration process, provision may be made for the registration (e.g., when using surface data sets that each describe the whole surface) to take place successively at various resolution levels (e.g., segmenting superficial tissue structures as surface features) and/or for recording a plurality of first surface data sets and/or a plurality of second surface data sets using different modalities. All of the surface data sets are used for the purpose of registration (e.g., successively from coarser resolution to finer resolution).

In an exemplary embodiment, macroscopic tissue structures may first be segmented in the surface data sets. Such macroscopic tissue structures may be fat regions and/or muscle fibers, for example. This takes place both at the resectate and at the extraction region. Based on these segmentations, a first approximate registration, for example, that may then be improved or refined in one or more further acts based on finer resolutions or structures (e.g., down to microscopic tissue structures) may be performed.

It can also be beneficial in other cases to perform the registration successively or even simultaneously on a plurality of size scales since, particularly at the level of very small (e.g., microscopic) surface features, the registration may also fail at many points. This is because there is often no smooth incision with a sharp scalpel between resectate and remaining tissue during the resection, and instead, a piece-by-piece excavation of a thin intermediate tissue layer may take place (e.g., using a suction instrument). Accordingly, it may occur that very small structures do not have an analog on the respective other side.

For the purpose of registration, the resolutions of the first surface data set and the second surface data set requiring registration may also be adapted to each other (e.g., by digital scaling), or registration data sets of different resolutions may routinely be generated from the first surface data set and the second surface data sets, and then registered with each other successively or even simultaneously in each case, using registration data sets of the same resolution in each case. If a plurality of first and/or a plurality of second surface data sets are used, it may, however, already be the case generally that first and/or second surface data sets of different resolutions are available, so that, for example, the more coarsely resolved surface data sets may be tried first, and the more finely resolved surface data sets may then be tried. A high-resolution first surface data set may, for example, be obtained from an ex vivo scan appliance. A coarsely resolved second surface data set relating to the extraction region may, for example, be obtained (e.g., from the camera of a laparoscope). Excellently resolved sectors may be obtained using a biopsy tool. In this case, an approximate registration may first be effected based on more coarsely resolved second surface data set, and then localization of the sectors may be attempted to thereby increase the quality and accuracy of the registration.

As mentioned above, cell structures and/or cell types and/or cell arrangements and/or cell clusters and/or fiber structures of the tissue and/or vascular structures of the tissue and/or spectral reflectivities of the tissue and/or the distribution of a fluorescent dye in the tissue and/or the distribution of malignant changes on the visible tissue surface and/or traces of an intervention instrument (e.g., a scalpel and/or a suction device and/or an energy instrument) may be used as surface features for the purpose of registration in the context of the present embodiment.

In a development (e.g., using at least one filtering algorithm and/or smoothing algorithm and/or edge highlighting algorithm), the surface features in different resolution regions of the surface data sets may be detected and/or combined into fingerprint data sets that are compared for the purpose of registration. Filtering algorithms, smoothing algorithms and/or edge highlighting algorithms (e.g., edge sharpening algorithms) and/or frequency analysis, for example, may be used to derive the tissue structures on various size scales in a preprocessing step. Specific surface features are derived from this preprocessed data, and the spatial registration may take place based on the surface features in a further act. The entirety of the surface features and/or their spatial arrangement (e.g., also in a part-region/sector of the surface) may be designated as a fingerprint, and fingerprint data sets may therefore be determined in the context of the present embodiments (e.g., on different size scales).

In order then to perform a registration between the tissue surface of the resectate and the tissue surface of the remaining tissue, fingerprint data sets of the first surface data set may, for example, be compared with fingerprints of the second surface data set. A spatial assignment and hence registration may be determined based on the greatest agreement. In the context of the present embodiments, when comparing fingerprint data sets, a plurality of correspondence candidates exhibiting significant agreement of the surface features may be output. If this occurs on various size scales, for example, a registration result may be obtained in a reliable way. By virtue of the assignment of fingerprints or hash values that are calculated therefrom for tissue sections, it is possible to economize computing capacity relative to a direct image-based comparison.

When using a digital biopsy tool, for example, for the purpose of registration in the case of a second surface data set that only presents the surface of the extraction region resulting from the resection in a sector-based manner, provision may be made for fingerprint data sets having the size of the sector and/or nine times the size of the sector to be generated and compared with a fingerprint data set of the sector. For example, the fingerprint of a sector-based measurement (e.g., using the digital biopsy tool) on the remaining surface may then be compared with the fingerprints determined for the resectate. Comparable size scales are appropriately applied as part of this activity, possibly also in a plurality of acts, in order first to determine which larger region the sector may be situated in, so that the sector may then be localized more accurately there. By repeating the procedure over a plurality of sector-based measurements at the remaining tissue surface in the extraction region, it is then possible, by geometric correlation of the various correspondence candidates, to obtain the correct registration result.

When using fingerprint data sets, a degree of abstraction is involved, and therefore, this procedural approach is particularly suitable for different modalities. Provision may therefore be made for the first surface data set and the second surface data set to be recorded using different modalities when fingerprint data sets are used. For example, the first surface data set may be recorded using optical coherence tomography, and the second surface data set may be recorded using optical confocal microscopy, etc.

According to a further development, when registering the surface data sets, use is made of an artificial intelligence registration algorithm (e.g., a deep neural network (DNN)) that has been trained using annotated surface data sets as training data. In this case, the artificial intelligence registration algorithm may, for example, generate fingerprint data sets and/or perform the comparison of fingerprint data sets, as described above. In an embodiment, with reference to annotated example data sets, an artificial intelligence registration algorithm (e.g., a DNN) may be trained to perform the assignment of sections of the tissue surface of the resectate and the extraction region based on image information/surface features, and to perform a registration on this basis. The artificial intelligence registration algorithm may be able to autonomously learn which surface features are advantageous for a registration (e.g., the registration algorithm learns to form a suitable tissue fingerprint data set that is then used for the purpose of registration). It is also possible in this case to perform the previously cited preprocessing acts (e.g., the application of filtering, smoothing, and/or edge highlighting algorithms and/or frequency analysis). A suitably trained artificial intelligence registration algorithm is nonetheless then used to derive the surface features (e.g., the fingerprint data sets), whereupon the comparison may then take place.

For example, use of an artificial intelligence registration algorithm may result in the following sequence of acts: preprocessing the first surface data set and the second surface data set (e.g., by using at least one filter algorithm and/or at least one smoothing algorithm and/or at least one edge highlighting algorithm and/or a frequency analysis; using the artificial intelligence registration algorithm to derive fingerprint data sets from the preprocessed first and second surface data sets; and comparing fingerprint data sets in order to find corresponding fingerprint data sets and hence corresponding surface features from which the registration result is determined.

As indicated above, the basic assumption of a similarity of corresponding surface features may result in errors, providing that the procedural approach of performing the registration based on (e.g., purely) corresponding surface features in surface data sets recorded following the separation of resectate and remaining tissue suffers from the weakness that, owing to the deployment of intervention instruments (e.g., laparoscopic energy instruments and/or tissue-suction intervention instruments), there is often a distinct tissue gap between the tissue surface resulting from the resection and the surface of the resectate. Although tissue properties extending over some distance (see also the examples cited above) still allow an assignment to be made, this is nonetheless hampered in the case of large and continuous tissue gaps and in the case of tissue regions that have been burned by energy instruments over a large area. For example, the remaining tissue surface in the extraction region is routinely cauterized using an energy instrument in order to permanently stop hemorrhaging. In this case, difficulties arise when using image-based methods that allow a registration based on similarities of surface structures. A second fundamental approach of the present embodiments, which is described in greater detail below, therefore offers a registration approach or a registration aid that may assign the corresponding locations on the resectate and the remaining tissue to each other, even though the two surfaces at the corresponding locations appear neither microscopically nor macroscopically sufficiently similar.

In order to achieve this, for the purpose of supporting the registration, an advantageous development of the present embodiments provides for generating a correspondence data set containing correspondence pairs of reciprocally corresponding surface features. Monitoring images of the current work region are continuously recorded by the recording instrument or a further recording instrument during the resection of the resectate. Upon detection of the performance of an incision, surface features of the respective resulting surfaces on both sides of the incision are detected by automatic evaluation of the corresponding monitoring images. Surface features that correspond to each other in geometric terms relative to the incision are assigned to each other in order to generate a correspondence pair. Each correspondence pair is stored in the correspondence data set, together with feature information describing the surface features of the correspondence pair, including, for example, a part-image of at least one monitoring image. The part-image shows at least the surface feature.

In this case, the monitoring images may be individual frames of a monitoring video that is recorded using the recording instrument or the further recording instrument during the resection of the resectate. The fundamental idea of this procedure is, therefore, to generate, from a monitoring video or monitoring images of the resection that may be recorded by, for example, a laparoscope or an operation microscope, a correspondence data set between resectate and remaining tissue, together with feature information that has been entered in each case. This correspondence data set is then used to register locations on the surface of the resectate with corresponding locations on the remaining tissue surface resulting from the extraction of the resectate in the extraction region.

The monitoring images may be recorded using a or the recording instrument (e.g., a laparoscope and/or an operation microscope and/or a camera of an illumination device). The monitoring images may be recorded using a stereo camera, where a three-dimensional surface structure of the resulting surfaces is determined and used for the detection and/or description and/or positional specification of at least one surface feature. Whereas a monoscopic (e.g., two-dimensional) video or two-dimensional monitoring images are adequate in principle for the procedure described, a stereo monitoring video or stereo monitoring images generally may be advantageous for greater reliability.

The actual performance of the resection is not part of the method described here. The evaluation of the monitoring images recorded during the resection of the resectate may in principle take place during the resection, but may also take place after the resection is complete. This provides that, for example, a monitoring video and/or a series of individual monitoring images may be selectively evaluated after completion of the resection in order to generate the correspondence data set. Various embodiments may be provided as an intervention tool or intervention instrument for performing the resection, where the intervention tool or intervention instrument may, for example, excavate and/or separate tissue and/or cauterize tissue by the application of energy and/or heat.

The correspondence data set may be used in different ways during the registration. In one embodiment, at least a second surface data set, optionally also an additional first surface data set, may be produced from the correspondence data set as described in greater detail below, or for the registration to be established relatively directly. On the other hand, the correspondence data set may, however, also be a registration aid, specifically by ultimately providing an additional similarity criterion for surface features that appear different, such that despite a completely different appearance image in the imaging modalities of the first surface data set and/or the second surface data set, a similarity may be determined based on the correspondence stored in the correspondence data set.

In a development, when generating a new correspondence pair, provision may be made for determining a relative position to at least one further correspondence pair already contained in the correspondence data set and/or to a reference feature that is not part of a correspondence pair, by detecting at least one of the surface features of the further correspondence pair and/or the reference feature in a monitoring image that shows the surface features of the new correspondence pair. The relative position is stored in the correspondence data set. In this way, the arrangement of the surface features of the individual correspondence pairs relative to each other is known, and therefore, this known relative arrangement may likewise be used in the registration process. For example, it becomes possible to create a representation of the respective surfaces of the resectate and the remaining tissue in the extraction region, as described in greater detail below. In this case, a linking feature need not necessarily be the surface feature of another correspondence pair, as it is also possible to establish a link to one or more reference features. The reason for this is that the number of reliably identifiable correspondence pairs of corresponding surface features may be relatively small. It is therefore also possible for the purpose of defining a relative position to identify "one-sided" surface features that then allow a relative position to be defined, at least as long as a bridge to previously defined correspondence pairs may be created thereby. The correspondences of the one-sided surface features may then be geometrically interpolated accordingly on both sides (e.g., on the surfaces of resectate and remaining tissue). Reference features may also be used to determine whether a work stage/incision has taken place. Such reference features therefore also allow movement tracking of the tissue generally.

More generally, the embodiment described is based on the assumption that nearly all surgical steps involved in separating the resectate from the remaining tissue take place under observation using the monitoring images. In reality, this prerequisite is effectively satisfied since the person performing the resection wants to see what they are doing during the course of their actions, some of which are critical; moreover, any hemorrhaging should be minimized or stopped on both resulting surfaces.

An important element in the detection or identification of a new correspondence pair of surface features is, as described above, the possibility of geometric assignment in relation to the incision or severance, providing, in other words, that certain geometric criteria are to be satisfied. The corresponding surface features may, therefore, be situated on two different sides of the current or immediately preceding operating region of the intervention instrument. In addition, the corresponding surface features may geometrically satisfy the condition that they could, currently or in a sufficiently recent previous frame, have been separated by the instrument. A certain inaccuracy is acceptable, particularly with regard to registration on this basis alone, since tissue is typically excavated in a liberal manner around the identified region anyway in the case of a follow-up resection. Further geometry criteria may require similar distances from the current incision edge, at which the surfaces of the resulting resectate and the surface of the remaining tissue are therefore adjacent, and/or a symmetrical opposition relative to this incision edge.

If reference features are to be avoided as far as possible, if it is not the start of the resection, the new surface features of a new surface pair may not be situated too far away from previously identified surface features of an earlier correspondence pair (e.g., so that the previously identified surface features are still situated in the field of view of the corresponding recording instrument; still visible in the same monitoring image or at least may be associated therewith). Otherwise, as mentioned, the reference features may be deployed.

Provision may be made for those surface features relating to the resectate side in all correspondence pairs to form, in their respective arrangement, an additional first surface data set. Provision may be made for those surface features relating to the extraction region in all correspondence pairs to form, in their respective arrangement, the or one of the at least one second surface data set, or for surface data sets to be determined therefrom. As a result of establishing the relative position of correspondence pairs, it is ultimately already possible during the creation of the respective surfaces to effect a mapping of the corresponding surfaces. Surface data sets may also be derived from this mapping accordingly. Locations of these surfaces that correspond at least in a point-based manner are also already known from the correspondences shown by the correspondence pairs.

In this context, based on the correspondence pairs and their respective relative position, provision may most advantageously be made for creating surface models of the surfaces of the extraction region resulting from the resection and of the resectate. At least part of the feature information and/or portions of at least one monitoring image showing the corresponding surface region are assigned to the surface models in a positionally accurate manner in order to determine respective surface maps, such that correspondence information assigning locations on the surface maps to each other is established by the correspondence pairs. The resulting surface maps may already constitute a further first and/or the second surface data set, for example. Accordingly, the correspondence information may be part of the registration result or, for example, may, in extended form, be the registration result, as explained below.

As part of the evaluation of the monitoring images, a textured surface map is therefore generated or updated in the case of new correspondence pairs, specifically a surface map respectively of resectate and the remaining tissue in the extraction region. In this case, broadly speaking, the surface patterns/surface images are derived from the monitoring images and assigned to the locations of the corresponding surface features or to the intermediate spaces between the surface features. The surface features of the correspondence pairs then have, as per the introductory description of the correspondence, the coordinates $a_R$ or by on these surface maps of resectate and remaining tissue. In a development of this, provision may also be made for a plurality of portions of different monitoring images to be averaged and used as a texture. The portions show the corresponding surface region. This provides that the textured surface of the surface models/surface maps may also be created using a plurality of monitoring images (e.g., a plurality of frames of a monitoring video; by averaging over a plurality of monitoring images). The textured surface maps may be established two-dimensionally or, for example, three-dimensionally when using a stereo camera.

In such an embodiment, the correspondence pairs are therefore stored with the surface features, the textured surface maps, and optionally further information in a data store.

In one embodiment, in order to expand the correspondence information provided by the correspondence pairs, provision may also be made for further corresponding locations of the surface maps to be determined by interpolation in regions of the surface maps that are situated between the surface features of correspondence pairs (e.g., a correspondence mapping and/or correspondence table that is valid for the complete surface maps). A limited number of reliable surface correspondences between resectate and the extraction region were identified using the procedural approach described previously. It is therefore effective to interpolate or extrapolate the correspondences in an appropriate manner, so that as many locations as possible (e.g., every location) $a_R$ on the surface of the resectate may be assigned corresponding locations by on the surface of the remaining tissue in the extraction region. In this way, a complete registration mapping may be produced as correspondence information from the evaluation process for the monitoring images.

The correspondence information may be used in an effective manner for the purpose of localizing an indicative feature of the resectate, which has a position that is known on the surface map of the resectate, on the surface of the extraction region. In this case, the position is usually known initially in the first surface data set or a first surface data set, which does not correspond to the surface map of the resectate, and/or in the further image data set. The position in the surface map of the resectate may then be determined by registering the surface map of the resectate with the first surface data set, which does not correspond to the surface map of the resectate, and/or with the further image data set. The corresponding registration is significantly easier to perform because: first, the registration concerns one and the same surface; and second, surface features contained in the correspondence pairs (and possibly reference features) that are suitable for a registration are already known. First surface data sets and/or further image data sets that do not correspond to the surface map may be recorded using the ex vivo scan appliance, for example. Accordingly, the indicative feature may be, for example, a region in which malignant changes of the tissue are situated too close to the surface of the resectate.

In other words, it is possible to effect, for example, an image-based registration of a piece of the surface exhibiting evidence of, for example, tumor infiltration in histology with the surface map of the resectate. For example, a microscopy image of the surface may be scaled down correspondingly and then spatially assigned to the surface map in an image-based manner. The result is a location $a_R$ on the surface map. The location by of the extraction region corresponding to $a_R$ may then be specified by the correspondence information.

In one embodiment, when tracking the recording instrument or the further recording instrument for recording the monitoring images (e.g., in the context of stereoscopy), the monitoring images and hence the surface map of the extraction region are already present in the patient-related coordinate system. If this is not the case, it is possible to effect a registration (e.g., the performance of which can also be significantly more reliable in this case) of the surface map of the extraction region with the second surface data set or with a further second surface data set that does not correspond to the surface map of the extraction region. It is therefore possible, for example, to effect an image-based registration between the textures of the surface map of the remaining tissue, possibly restricted to a region around the location $b_V$, and a current image (e.g., still a monitoring image) of the recording instrument and/or the further recording instrument and/or yet another recording instrument (e.g., the current video image of the laparoscope). This allows the surface section of the remaining tissue that corresponds to the, for example, tumor-infiltrated surface section of the resectate to be displayed (e.g., as an overlay, augmented reality, or markings in the navigation system), as explained in detail above in relation to the support measures. As an alternative to an image-based registration relating to a depiction as a support measure, it is also possible, as suggested above, to effect the registration using a navigation system. The whole surface map of the remaining tissue in the extraction region is registered with the intraoperative geometry (e.g., the patient-related coordinate system).

The detection of the performance of the incision may take place in a manner that is at least partially image-based in the monitoring images (e.g., by tracking previously detected surface features and/or an intervention instrument that is visible in the monitoring images, with regard to a tissue contact, and/or based on supplementary information that is assigned to the monitoring images relative to time). It is therefore possible, using all the available information, to determine whether the intervention instrument or intervention tool is currently separating, removing, or processing tissue, or whether the intervention instrument is currently not performing an action on the tissue. This may take place for every monitoring image (e.g., every frame in a monitoring video), such that the identification of new corresponding surface features may only be carried out if, in the current monitoring image or in a very recently recorded monitoring image, the intervention instrument performed an action on the tissue resulting in a further separation of resectate and tissue (e.g., due to excavation or incisions). For example, the intervention instrument that is visible in the monitoring images may therefore be used as a type of indicator with regard to the applicability of generating new correspondence pairs. Instruments are also already easy to detect in the context of corresponding image processing.

The supplementary information may be determined so as to describe a movement of the intervention instrument as detected by a or the navigation system, and/or a supply of energy to the intervention instrument as triggered, for example, by operation of a foot pedal, and/or a workflow step of an intervention workflow. For example, provision may be made in this case for the monitoring images (e.g., the monitoring video) to be annotated using external information sources or manually. For example, as is known in principle from the prior art, it is possible to use an optical navigation system that tracks the progress of the resection. Support devices that are able to identify a phase of the resection by workflow analysis have also been provided previously. For example, such workflow analyses may also evaluate the actual monitoring images, such that specific sections of the resection may be identified from a monitoring video of the operation, for example.

With regard to the workflow act, such supplementary information may also be used for the basic preselection of monitoring images to be evaluated or of the corresponding section of the monitoring video. Since it is then only necessary to evaluate the monitoring images that show material that is actually relevant, the burden is reduced.

A further relevant information source in relation to the possible annotation of monitoring images or monitoring videos is an operating appliance (e.g., a foot pedal), via which the intervention instrument may be supplied with electrical energy, for example. It may be assumed that an energy supply is only activated by the person performing the intervention when processing of the tissue is to take place.

As indicated above, the surface features of a new correspondence pair may be selected such that the surface features may be detected with a reliability that exceeds a threshold value in a respective imaging modality of the surface data sets and/or of at least one further image data set.

This is particularly appropriate if an image-based registration is to take place based on the surface maps (e.g., also as surface data sets), with, for example, further surface data sets and/or further image data sets (e.g., from an ex vivo scan appliance and/or from a recording instrument deployed in the extraction region). In this case, use is made of the fact that it is generally known which modalities are used in the context of the resection. The physical imaging properties of these imaging modalities are likewise known, and therefore, it is also known which surface features may be identified, with what degree of reliability and using which imaging modality, such that the selection of the surface features for the correspondence pairs may take place in a correspondingly foresighted manner.

In a development, provision is made for the surface features of the correspondence pairs to be tracked in the monitoring images over the resection time period for as long as the surface features are contained in the monitoring images. If a subsequent change of the surface feature by the intervention instrument or a further intervention instrument (e.g., an energy instrument) is detected, the feature information for describing the changed surface feature is adapted. Alternatively or additionally, if a one-sided change in the surface is detected as a result of automatic evaluation (e.g., image evaluation relating to the region of change in a monitoring image that was recorded before the change and/or based on information about the relative position), changed surface features of correspondence data sets are found, and the associated feature information for describing the changed surface feature is adapted. The term "one-sided" may be that either only the surface of the resectate or only the surface in the extraction region (e.g., the surface of the remaining tissue) is affected. It may occur in the case of resections that a part of the tissue surface of the future resectate or of the future remaining tissue is processed again subsequently (e.g., hemorrhaging is stopped by cauterization using an energy instrument). It is possible to identify such locations or regions of change because the surface features situated around the instrument are either all on the side of the resectate or all on the side of the extraction region. The surface textures at the corresponding positions change in such cases, so that if a surface feature of a correspondence pair is situated there, the corresponding feature information may be adapted. With regard to the generation of a surface map, it is then also possible appropriately to update the textures derived from the monitoring images in the region of change. Overall, therefore, the correspondence pairs and, for example, the surface maps likewise are continuously updated in this way, because changes that occur subsequently are taken into consideration. In other words, whenever one-sided processing of tissue subsequently takes place in a region of change, feature information or the surface textures of surface maps are adapted and updated again. The respective locations/positions of the correspondence pairs are nonetheless left unchanged. This also has a particular advantage in comparison with a purely image-based registration of the first and second surface data sets, in that particularly when such one-side changes in the tissue surface are effected subsequently, similarities may be eliminated, and purely image-based approaches to images recorded after completion of the resection may come to nothing.

An embodiment of the method may also be formulated more generally as a method for the navigational support of a person performing a resection on a patient following extraction of a resectate, for navigation relative to the resectate in the extraction region. The method includes generating a correspondence data set containing correspondence pairs of reciprocally corresponding surface features. Generating the correspondence data set includes continuously recording monitoring images of the current work region by a recording instrument during the resection of the resectate. Upon detection of the performance of an incision, surface features of the respective resulting surfaces on both sides of the incision are detected by automatic evaluation of the corresponding monitoring images. Surface features that correspond to each other in geometric terms relative to the incision are assigned to each other in order to generate a correspondence pair. Each correspondence pair is stored in the correspondence data set, together with feature information describing the surface features of the correspondence pair, including, for example, a part-image of at least one monitoring image. The part-image shows at least the surface feature. When generating a new correspondence pair, a relative position to at least one further correspondence pair already contained in the correspondence data set, and/or to a reference feature that is not part of a correspondence pair, is determined by detecting at least one of the surface features of the further correspondence pair and/or the reference feature in a monitoring image that shows the surface features of the new correspondence pair. The relative position is stored in the correspondence data set. Based on the correspondence pairs and the respective relative position, surface models of the surfaces of the extraction region resulting from the resection and of the resectate are created. At least part of the feature information and/or portions of at least one monitoring image showing the corresponding surface region are assigned to the surface models in a positionally accurate manner in order to determine respective surface maps, such that correspondence information assigning locations on the surface maps to each other is established by the correspondence pairs. A first surface data set of the resectate is recorded using an ex vivo scan appliance. The first surface data set of the resectate is registered with the surface map of the resectate (may be considered as a further first surface data set) and thus, using the correspondence information, with the surface map of the extraction region (as the second surface data set). At least one support measure that supports the navigation in the extraction region relative to the resectate is performed using the registration.

In addition to the method, the present embodiments also relate to a support system for the navigational support of a person performing a resection on a patient following extraction of a resectate, for navigation relative to the resectate in the extraction region. The support system includes a control entity configured to perform the method of one or more of the present embodiments. All the explanations relating to the method may be transferred analogously to the support system, from which the previously cited advantages may therefore likewise be derived.

The support system may include, for example, diverse instruments, an ex vivo scan appliance, a navigation system, and the like. The instruments may include, for example, recording instruments and/or intervention instruments. The support system may also include a display appliance (e.g., for the output of depictions in the context of support measures), just as an augmented reality appliance is additionally or alternatively conceivable. The control entity may be configured accordingly for the purpose of activating all of these conceivable components. For example, the control entity may have at least one processor and at least one storage device (e.g., data store). Corresponding functional units may be provided in the control entity in order to execute the acts of the method.

For example, the control entity may have at least one interface for receiving the first and/or the second surface data set, a registration unit for registering the surface data sets, and a support unit for performing the at least one support measure. Further functional units may also be provided for further embodiments as per the explanations relating to the method of one or more of the present embodiments.

A computer program according to the present embodiments may be loaded directly into a storage unit of a control entity of a support system, and has program means for executing the acts of a method according to the present embodiments when the computer program is executed in the control entity of the support system. The computer program may be stored on an electronically readable data medium (e.g., a non-transitory computer-readable storage medium) that therefore includes electronically readable control information that is stored thereon. The control information includes at least one computer program according to the present embodiments and is configured so as to perform a method according to the present embodiments when the data medium is used in a storage entity of a support system. The data medium may be a non-transient data medium such as, for example, a CD-ROM.

BRIEF DESCRIPTION OF THE DRAWINGS

FIG. 8 shows a schematic monitoring image at a later time point during the resection;

FIG. 9 shows a schematic monitoring image at an even later time point during the resection;

DETAILED DESCRIPTION

Exemplary embodiments are explained in greater detail in the following, where a resection of a tumor from an organ of a patient is considered as an example of a resection. In the context of such a tumor resection, it is of interest to know whether an R0 resection has taken place, and thus whether tissue exhibiting malignant change (e.g., tissue that has been infiltrated by tumor cells) remains in the patient. It is therefore beneficial for the person performing the resection not only to have histological results indicating whether tumor cells or other malignant residues are still present on or near the surface of the resectate, but also correspondingly to assign this information spatially in the extraction region (e.g., to the remaining tissue surface resulting from the resection). In the context of the current description, the cited presence of a malignant change in the resectate in a defined proximity to the surface of the resectate is also intended to include the malignant change being present directly at the surface of the resectate.

Figure 1:
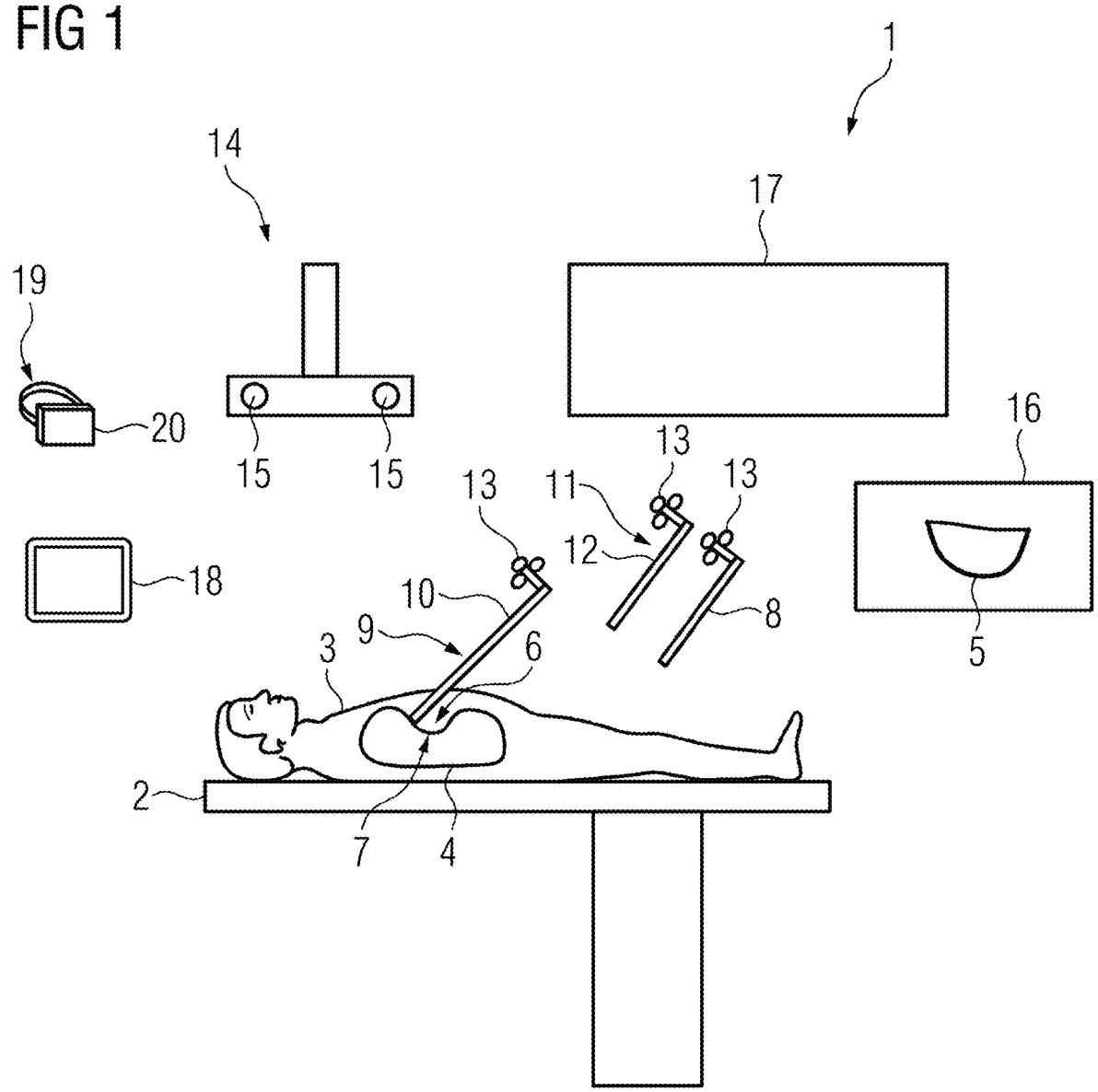
FIG. 1 shows an exemplary embodiment of a support system.

FIG. 1 shows a schematic diagram of one embodiment of a support system 1 that is suitable for performing a tumor resection and a method according to an embodiment.

The patient 3, within whom a resectate 5 has already been extracted from an organ 4, is shown on an operating table 2. A tissue surface 7 resulting from the resection remains in an extraction region 6 accordingly. A number of different instruments in the support system 1 are available to the person performing the resection, where an intervention instrument 8, a first recording instrument 9 in the form of a digital biopsy tool 10, and a second recording instrument 11 in the form of a laparoscope 12 with a stereo camera are shown purely by way of example. All instruments 8, 9 and 11 and, optionally, further instruments not shown have markers 13 for an existing optical navigation system 14, of which the cameras 15 are also shown. These may be ceiling-mounted, for example. As an alternative or in addition to the optical navigation system 14, an electromagnetic navigation system may also be used. The current position and orientation (e.g., the pose) of all instruments in use may be determined in a patient-related coordinate system by the navigation system 14. For example, the recording positions at which recordings are produced by imaging appliances (e.g., cameras and/or OCT sensors) of the recording instruments 9, 11 are therefore also known.

The laparoscope 12 may have, for example, a stereo camera by which monitoring images may also be recorded during the intervention. The digital biopsy tool 10 may have, for example, a microscope and/or an OCT sensor in order to record a small sector of, for example, 0.01 to 10 mm$^2$ in size.

The support system 1 further includes an ex vivo scan appliance 16 that may also be referred to as a digital histology device. The resectate 5 is already placed in the ex vivo scan appliance 16, so that the surface of the resectate 5 may be scanned there over a large area (e.g., in order to identify surface regions in which malignant changes are still present, such as tumor cells).

The examination system 1 also has a control entity 17 that may maintain a communication connection to all of the other components (e.g., the ex vivo scan appliance 16, the instruments 8, 9 and 11, the navigation system 14 as well as further components). For example, the control entity 17 also has access to a display appliance 18 and an augmented reality appliance 19 (e.g., an augmented reality headset 20) that may be activated for support measures.

For example, the control entity 17 is configured to perform the method, exemplary embodiments of which are illustrated in greater detail in the following.

Figure 2:
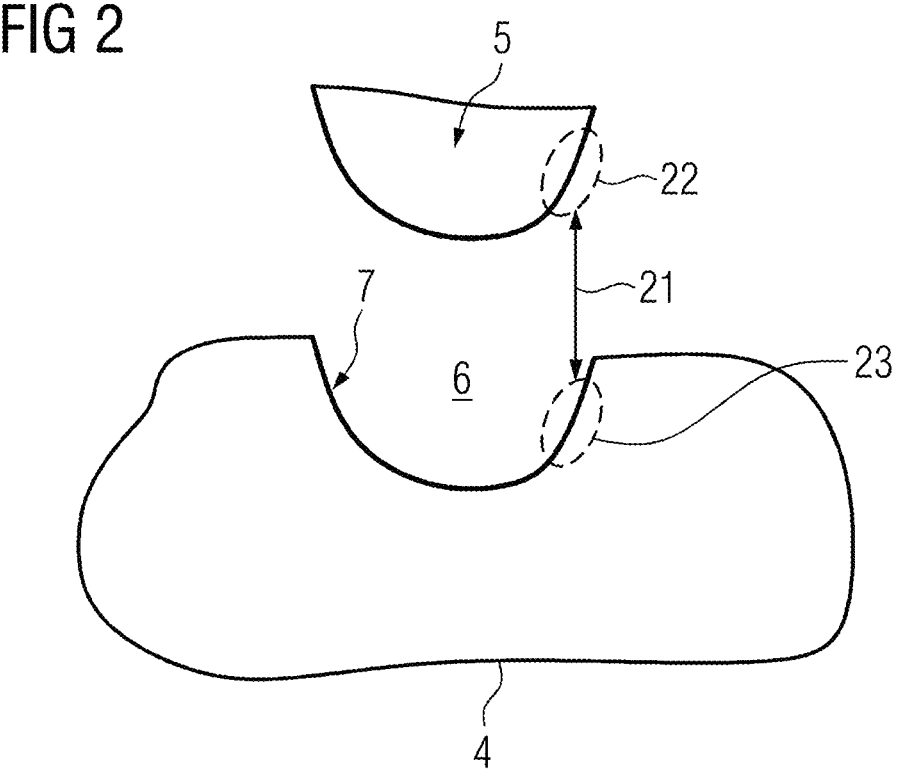
FIG. 2 shows a diagram of an exemplary correspondence of locations on the resectate and locations on the remaining tissue surface.

The aim of the method according to the present embodiments, as indicated more clearly in FIG. 2, is to establish a registration indicated by the arrow 21. The registration allows, for example, surface regions/locations 22 on the resectate 5 that have been identified as infiltrated by tumor cells to be found again on the remaining tissue surface 7 in the operation geometry (e.g., in the patient-related coordinate system), whereby the corresponding location 23 on the remaining tissue surface 7 in the extraction region 6 may be found automatically, and allows the person performing the resection to find this location 23 as easily as possible using suitable support measures.

Figure 3:
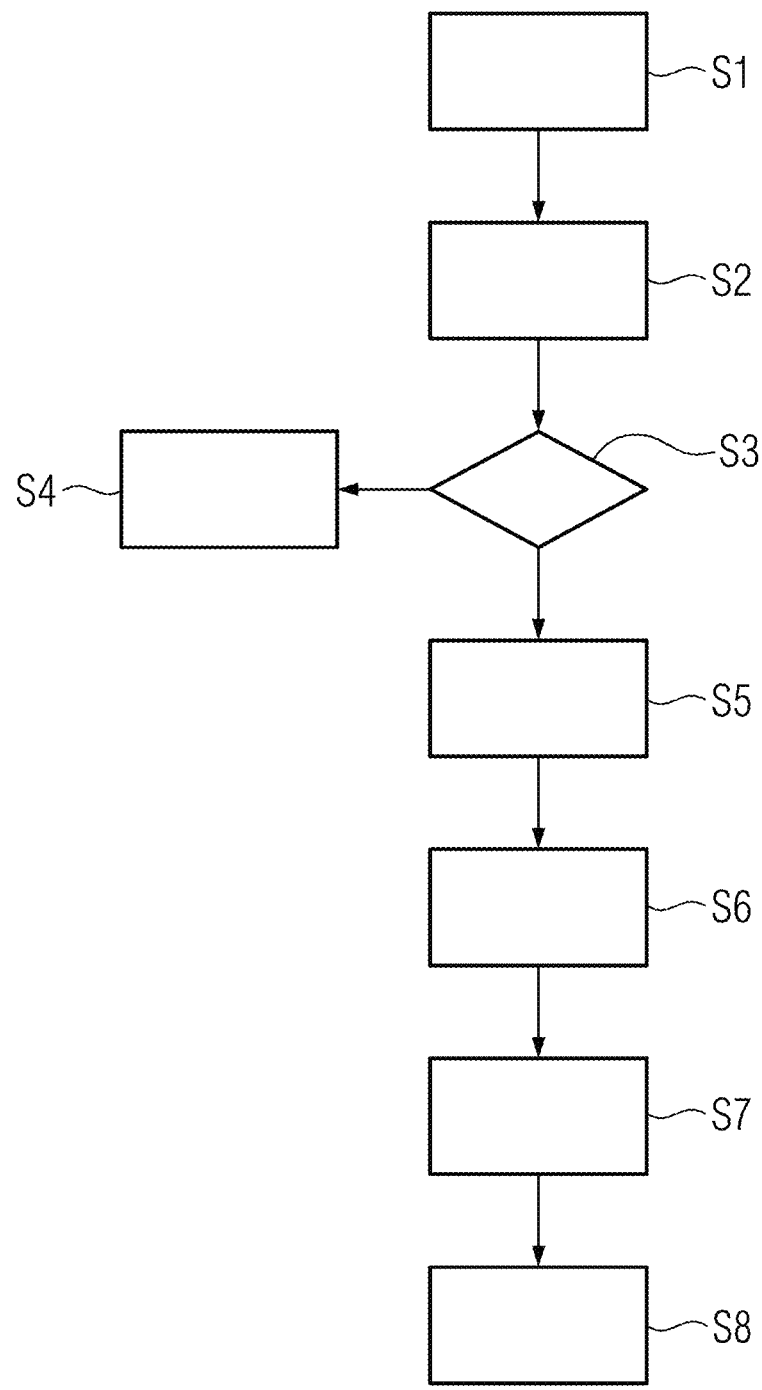
FIG. 3 shows a flow diagram of a first exemplary embodiment of a method.

FIG. 3 shows a flow diagram of a first exemplary embodiment of the method. In act S1, the resectate 5 is scanned in relation to a surface of the resectate 5 in the ex vivo scan appliance, providing that a first surface data set of the resectate 5 is recorded by the ex vivo scan appliance. This first surface data set of the resectate 5 is automatically evaluated in act S2 in order to check whether a malignant change is present in the resectate 5 in a defined proximity to the surface of the resectate 5 (e.g., not separated from the surface of the resectate 5 by more than a safety distance). Locations at which this is the case are marked as indicative features. As an alternative to the first surface data set or in addition to the first surface data set, a further image data set from the ex vivo scan appliance may also be evaluated.

In act S3, it is checked whether malignant changes (e.g., the infiltration by tumor cells) were detected. The method is terminated in act S4 if this is not the case. If indicative features are, however, present, a plurality of sectors of the remaining tissue surface 7 are recorded in act S5 using the digital biopsy tool 10 (e.g., one to five sectors) as a second surface data set of the extraction region 6. The sectors may be recommended to be evenly distributed in this case; however, it is also possible to output a rough indication, based on analysis of the first surface data set, of where a particularly high number of easily identifiable surface features are present as a recommendation to the person performing the resection. The relative positions of the recorded sectors of the remaining tissue surface 7 are known by virtue of the navigation system 14.

In act S6 of this first exemplary embodiment, the first surface data set and the second surface data set are now registered with each other, specifically by finding reciprocally corresponding surface features at the surface of the resectate 5 and at the remaining tissue surface 7. This is possible because the microscopic and macroscopic cell structure or tissue structure at a location of the resectate and at a corresponding location of the remaining tissue surface 7 may exhibit strong similarities, since they were originally joined together. Examples of such similarities include patterns in the arrangement of cells, tissue boundary layers, blood vessels, tissue densities, and cell types, and possibly the infiltration pattern of tumor cells. This fact is fully utilized in that candidates for corresponding surface features including geometric alignment are identified by algorithmic correlation of the small-surface image data that is measured in a sector-based manner by the digital biopsy tool 10 with the large-area image data from the ex vivo scan appliance 16.

In this first exemplary embodiment, for the registration in the act S6, use is also made of an artificial intelligence registration algorithm, for example. In this case, preprocessing using, for example, at least one filter algorithm and/or at least one smoothing algorithm and/or at least one edge highlighting algorithm and/or a frequency analysis is performed in a first part-step in order to derive tissue structures on various size scales. The first surface data set and the second surface data set thus preprocessed are then transferred to the artificial intelligence registration algorithm as input data. For example, a DNN may be used in this case. The DNN has been trained, with reference to annotated example data sets, to derive surface features that are advantageous for a registration from the preprocessed surface data sets and to assemble these surface features to form fingerprint data sets. A fingerprint data set describes the entirety of surface features and a corresponding spatial arrangement within at least a part-region of the surface described by the surface data sets. For example, with regard to the second surface data set, which is recorded using the digital biopsy tool, a fingerprint data set may be determined for each sector; further subdivisions may be effected within the sectors, and smaller fingerprint data sets may be generated for part-regions of the corresponding surface.

The fingerprint data sets of the first surface data set and the second surface data set are then compared with each other, on corresponding size scales, in order to find candidates for possible correspondences, also by applying similarity criteria in particular. A spatial assignment may be output based on the greatest agreement in this case, though it is optionally also possible to output a plurality of correspondence candidates exhibiting significant agreement of the surface features. By repeating this procedure over a plurality of sector-based measurements at the remaining tissue surface 7, the correct registration is then created by geometric correlation of the various candidates.

With regard to further exemplary embodiments that are discussed below and include second surface data sets covering a larger portion of the remaining tissue surface 7, execution on different size scales is advantageous (e.g., if as a result of excavating a thin layer of tissue situated between the surface of the resectate 5 and the remaining tissue surface 7, the registration at the level of the microscopic arrangement of cells would fail at many points). Accordingly, it is possible to work on a plurality of size scales. For example, it is possible to use fingerprint data sets on the size scale of the microscopic cell structures (e.g., 1 to 100 cells, on the size scale of several hundreds of cells, such as 100 to 1000 cells) and on macroscopic size scales.

As a result of using such fingerprint data sets, for example, this type of image-based registration may also be reliably applied to first surface data set and the second surface data set of different modalities (e.g., using optical coherence tomography for the first surface data set and sector-based scanning of the remaining tissue surface by optical confocal microscopy). In another example, the surface of the resectate 5 may be recorded over a large area using high-resolution microscopy, and the surface of the remaining tissue surface may be recorded by a lower-resolution laparoscope or operation microscope. In the case of other types of registration, it may again be appropriate, when using different modalities, to deploy an artificial intelligence registration algorithm that has been suitably trained for the combination of modalities.

Following completion of act S6, a registration result that allows locations on the surface of the resectate 5, which have a position in the coordinate system of the first surface data set that is known, to be assigned a location on the remaining tissue surface 7 is therefore available.

Because the sectors in this case are recorded using the digital biopsy tool 10, which is tracked by the navigation system 14, the position of the locations is then also known in the patient-related coordinate system of the navigation system 14.

This is applied to various possible support measures in act S7.

In act S7, a two-dimensional or three-dimensional tissue map or other presentation of the resectate 5 may be displayed on the display appliance 18 as a support measure, where the representation may be derived, for example, from the first surface data set and/or the further image data set from the ex vivo scan appliance 16. In this representation, which shows the surface of the resectate 5, the indicative features specified in act S2 (e.g., regions of malignant change) are highlighted in red. At the same time, the registration result of act S6 is used to display the relative position of the digital biopsy tool 10 and/or at least one other instrument (e.g., an intervention instrument 8) relative to these indicative features and hence, relative to the corresponding locations on the remaining tissue surface 7. In other words, it is ascertained based on the registration result which location on the remaining tissue surface 7 corresponds to the indicative feature; the position of the respective instrument relative to this location is determined by the navigation system 14, and based on this relative position, the relative pose of the instrument relative to the indicative feature is visualized with the representation of the resectate 5. In other words, while the instrument in real space is situated at a location or in the proximity of a location at the surface of the remaining tissue, the instrument is virtually incorporated at the corresponding location on the surface of the resectate 5, or the corresponding location/region is otherwise marked.

In another variant of such a support measure, the surface regions of the remaining tissue surface 7 that correspond to regions containing tumor cells on the surface of the resectate 5 may be displayed as augmented reality or on a virtual two-dimensional or three-dimensional surface model (e.g., with incorporation of the navigated (tracked) instruments).

An optional check may take place in act S8. Based on the support measures, the user is able, for example, to move the digital biopsy tool 10 to locations on the remaining tissue surface 7 that are displayed as possible regions containing tumor cells. By a measurement using the digital biopsy tool, the user is able to verify whether the displayed correspondence was determined correctly and, if applicable, to assess directly from the images of the digital biopsy tool whether tumor cells have also infiltrated on the remaining tissue side. A follow-up resection may then be performed if applicable (outside the method described here).

The check measurement in the optional act S8 may be fed back into act S6 in order to improve the registration. The acts S5 and S6 may also be repeated iteratively (e.g., if it is determined in act S6 that the quality of the registration result is too low). Surface data of the second surface data set may then be recorded using the digital biopsy tool 10 for at least one further sector in a repetition of act S5.

Figure 4:
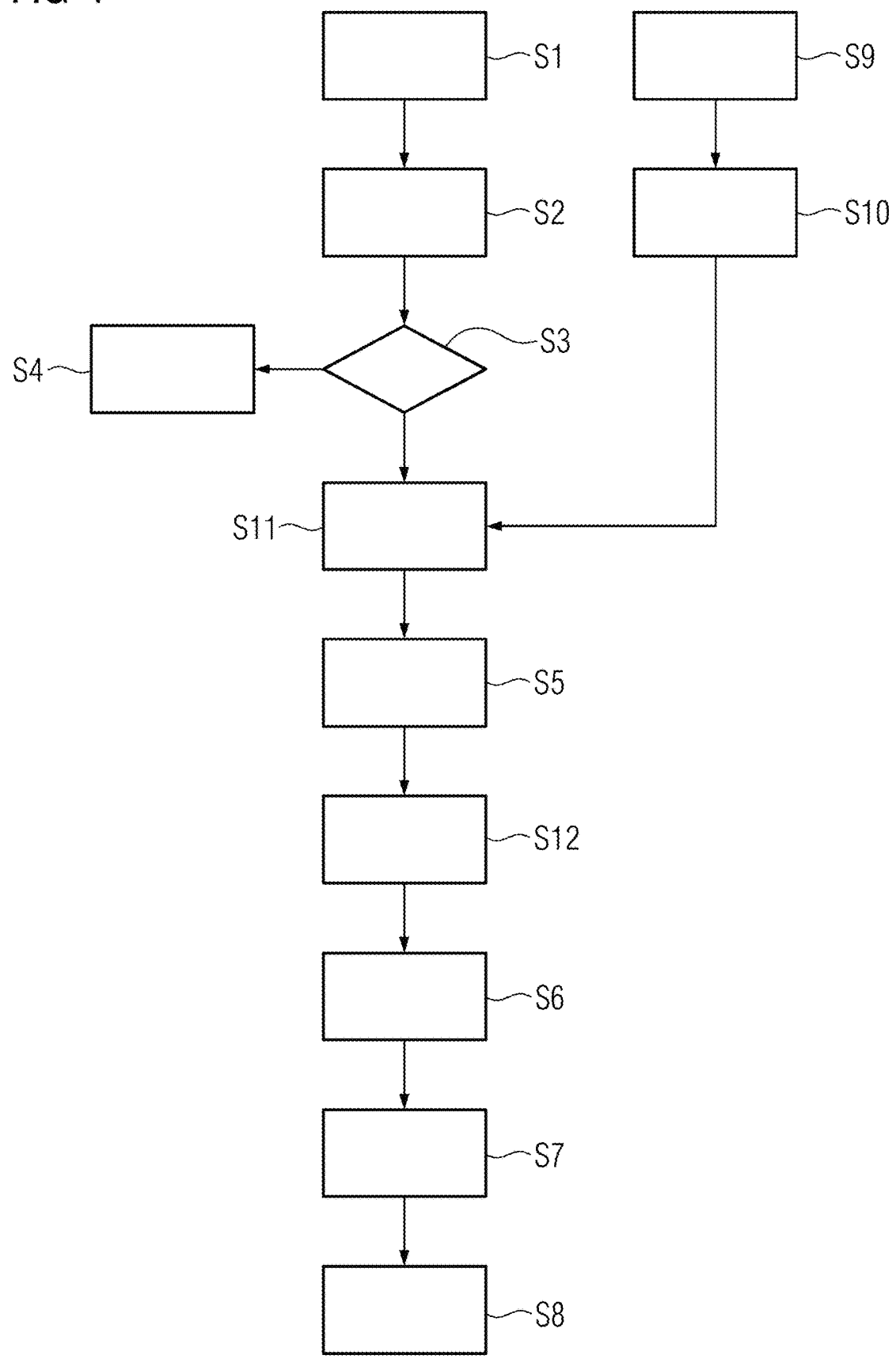
FIG. 4 shows a flow diagram of a second exemplary embodiment of the method.

FIG. 4 illustrates a second exemplary embodiment of the method. In the second exemplary embodiment, supplementary, intervening first and second surface data sets are used as a type of intermediate act in order to allow easier registration. Although the acts S1 to S4 remain essentially unchanged in this case, a survey of both the resectate 5 and the remaining tissue surface 7 in the extraction region 6 is performed in act S9 (e.g., even before the resectate 5 is positioned in the ex vivo scan appliance 16). For example, the laparoscope 12 or another recording instrument 11 (e.g., an operation microscope) may be used for this purpose. The resectate 5 may be rotated in front of the recording instrument 11, for example. With regard to the remaining tissue surface 7, partial data sets are also recorded in different orientations of the imaging sensor of the recording instrument (e.g., a stereo camera). Using the procedure described in US 2017/0105601 A1, for example, a three-dimensional surface model may then be generated in act S10 for both the resectate 5 and the extraction region 6 based on the partial data sets. If the image data of the partial data sets is now used as texture of this surface model, corresponding first and second surface data sets of the resectate 5 and the remaining tissue surface 7 in the extraction region 6 are produced in act S10.

Since the same surfaces are depicted, using suitable algorithms and possibly interpolation/smoothing for the purpose of image analysis, in act S11, the large-area scan result of the ex vivo scan appliance 16 as recorded in act S1 may be registered with the first surface data set of act S10 (e.g., based on macroscopic tissue structures that are contained both in the scan data from the ex vivo scan appliance 16 and in the image data from the stereo camera of the laparoscope 12). Markers (e.g., marking objects) arranged on the resectate 5 may also be used for ease of registration in act S11.

The registration act S6 may also be performed in parallel, before, or after act S11, and in this case, registers the first and second surface data sets recorded in act S10 with each other. The surface data sets are recorded using the same modality. It may nonetheless be beneficial to perform the act S6 after the act S11, since the first surface data set from the ex vivo scan appliance 16, which was recorded in act S1, may then likewise contribute to improving the registration. First surface data sets from two different modalities are then ultimately deployed in the registration act S6.

In act S12, the sectors that were recorded by the tracked digital biopsy tool 10 in act S5 are likewise registered directly with the second surface data set determined in act S10. This is particularly easy to perform since the latter is already present in the patient-related coordinate system of the navigation system 14, which also tracks the digital biopsy tool 10, as a result of using the recording instrument 11. If the act S6 is performed afterwards, these measurements may also be fed into the registration if applicable.

In the second exemplary embodiment, as per FIG. 4, the act S7 may then also offer support measures that are based on a visualization of the textured surface models as specified in act S10.

The third exemplary embodiment, as shown in Figure, 5 differs from the second exemplary embodiment in FIG. 4 in that the digital biopsy tool 10 is not used. The first and second surface data sets determined in act S10 are registered directly with each other, in a rigid or, for example, deformable manner. This is therefore effected based on geometric properties of the corresponding textures of the three-dimensional surface models generated from the stereo camera data. This provides that indicative features with infiltrated tumor cells identified by the digital histology device (e.g., the ex vivo scan appliance 16) may be assigned directly to corresponding locations on the remaining tissue surface 7. In the context of the present embodiments, the digital biopsy tool 10 may be used in order to provide a basis for the registration and to allow a check in the patient (cf., act S8).

Figure 6:
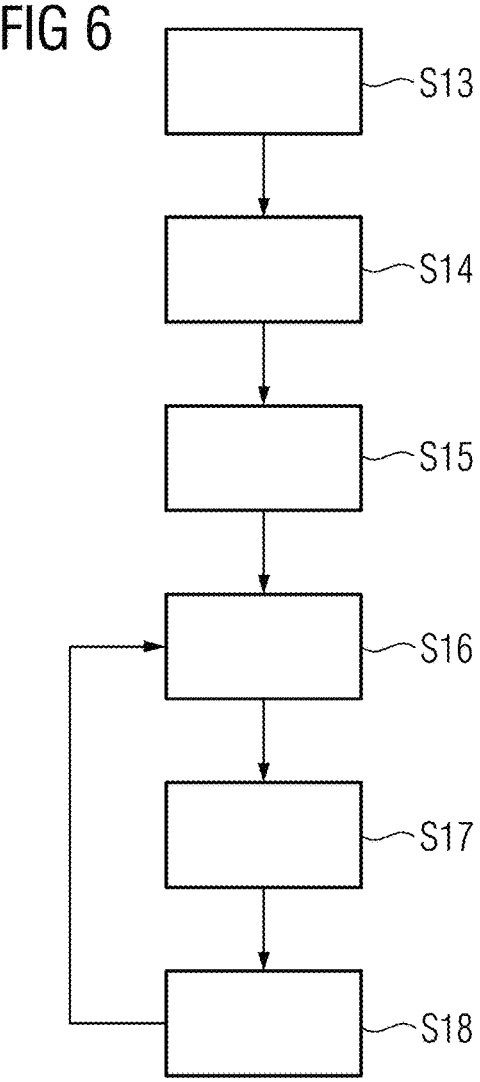
FIG. 6 shows a flow diagram for the creation of a correspondence data set from monitoring images.

In the respective acts S6 of the exemplary embodiments discussed, a correspondence data set that contains correspondence pairs of corresponding surface features may also be used, where the described similarity is not necessarily present. This provides that such a correspondence data set, the determination of which is explained by way of example in greater detail with reference to FIG. 6, also allows surface features to be related to each other that no longer bear any similarity, but would allow an image-based assignment in surface data sets recorded following completion of a resection. This may be the case, for example, because too great a tissue layer was removed meanwhile and/or a post-operative treatment (e.g., cauterization) was performed on one side. The correspondence data set may therefore provide an additional similarity criterion.

When determining the correspondence data set, use is made of the fact that nearly all surgical steps involved in the separation of the resectate 5 from the remaining tissue take place under observation (e.g., by a stereo camera such as the laparoscope 12), such that it will also then be assumed that a monitoring video having frames that depict individual monitoring images recorded in a temporally consecutive manner exists. Since such a monitoring video is usually annotated manually and/or automatically (e.g., in the case of an automatically determined workflow step), it is easy to select the relevant portion of the monitoring video that fully shows the resection of the resectate 5.

The fundamental idea is therefore to generate a correspondence data set between the surface of the resectate 5 and the remaining tissue surface 7 from a monitoring video or monitoring images of the resection (e.g., recorded by the laparoscope 12 or alternatively by an operation microscope). This correspondence data set may be used for the subsequent registration of locations 22 on the surface of the resectate 5 with corresponding locations 23 on the remaining tissue surface 7.

The evaluation of the monitoring images described here may already be performed in real time during the resection or afterwards based on the recorded monitoring video.

The evaluation starts in act S13, where a count variable jumps to the frame that characterizes the annotated/identified start time point of the resection within the monitoring video. This count variable is designated n in the following.

In act S14, the $n^{th}$ frame of the monitoring video is loaded as a monitoring image accordingly. In the case of a monitoring video recorded with a stereo camera, it is also possible in the act S2 to perform a stereo reconstruction of a three-dimensional surface map of the current scene using a method that is generally known from the prior art. The following acts are then executed either on the monitoring image of the frame or on the textured three-dimensional surface map of the current scene.

In act S15, the current monitoring image is analyzed in various ways (e.g., in order to determine whether an interaction of an intervention instrument 8 with the tissue actually took place). For this purpose, provision is first made for detecting and localizing the intervention instrument 8 within the monitoring image, where position information from the navigation system 14 relating to the intervention instrument 8 may alternatively or additionally be used. Using the available information, it is then determined whether the intervention instrument is currently separating, removing, or processing tissue or whether the intervention instrument is currently not performing an action on the tissue. For each frame in the relevant time period of the resection, this information is assigned to the corresponding monitoring image and stored. This information may be used, for example, to further reduce the number of frames or monitoring images requiring more precise analysis, since new correspondence pairs of surface features may only occur if the tissue is actually being influenced by the intervention instrument.

Those frames (e.g., monitoring images) that accordingly are to be processed are then consecutively analyzed in the series of acts starting from act S16, as described.

For a frame that is currently to be processed, following preprocessing as described above with reference to FIG. 3 to FIG. 5 if applicable, it is first attempted in the act S16 to find surface features of correspondence pairs that are already stored in the correspondence data set, therefore, to localize the surface features within the monitoring image. The same applies to the reference features, which are optionally used if applicable. This does not apply if no correspondence pairs have yet been determined. It is also attempted in the act S16 to find new corresponding surface features. As mentioned above, this method act is only executed for a monitoring image if, in the current frame or in a very recent frame, the intervention instrument performed an action on the tissue resulting in a further separation of resectate 5 and remaining tissue (e.g., due to excavation or incisions or other change of the tissue).

As candidates for corresponding surface features, image analysis may be used here to select candidates that were not yet sufficiently analyzed in previous monitoring images, but also candidates that are equally clearly identifiable, at least in the imaging modalities of the ex vivo scan appliance 16. Further imaging modalities may include imaging modalities of recording instruments 9, 11. With respect to such a surface feature, a geometrical check determines whether an actually matching surface feature may be found on the "other side". In other words, the current incision edge or separation edge marks the boundary between tissue that will form the surface of the resectate 5 and tissue that will form the remaining tissue surface 7 of the extraction region 6. Corresponding surface features should lie on two different sides of this separation edge and geometrically satisfy the condition that the surface features could, currently or in a sufficiently recent previous frame, have been separated by the intervention instrument 8. If this is not the start of the resection, the new surface features should adjoin previously identified surface features, providing that the previously identified surface features should not be too far away. When performing such a check of the relative position of surface features that already form part of a correspondence pair, and of reference features if applicable, this relative position may also be stored immediately if a new correspondence pair is actually found, since these relative positions of surface features (e.g., possibly reference features) to each other are used subsequently in the procedure. During this identification of corresponding surface features, it is also possible (e.g., in addition to the geometric considerations) to perform similarity tests, as described above (e.g., to create and compare fingerprint data sets).

If a new correspondence pair is found in act S16, this is stored as part of the correspondence data set, together with feature information (e.g., at least that portion of the monitoring images that show the surface feature), but also further feature information if applicable. Further feature information, for example, may take the form of a fingerprint data set of the surface features (e.g., when using the correspondence data set to support a registration as per the acts S6).

Specifically, in this exemplary embodiment, for each correspondence pair that is found, a surface map is extended, as described in greater detail below.

An illustration of this continuous process for finding correspondence pairs of corresponding surface features, it being possible likewise to use the surface features discussed previously, is explained in greater detail with reference to FIG. 7 to FIG. 9, which schematically show exemplary monitoring images at different time points (e.g., different frames of a monitoring video).

Figure 7:
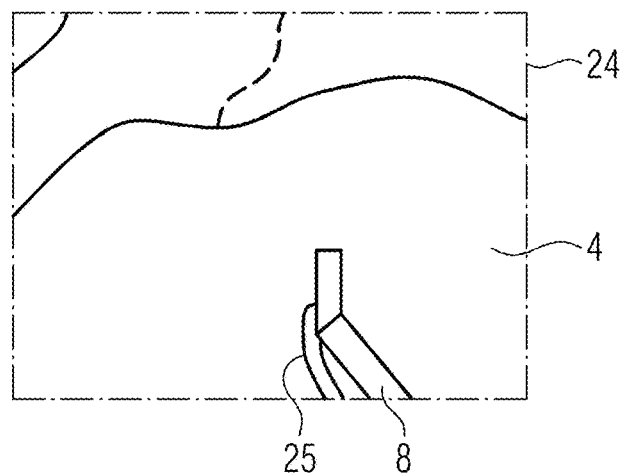
FIG. 7 shows a schematic monitoring image at the start of a resection.

FIG. 7 schematically shows a monitoring image 24 at the start of the resection. Visible are an intervention instrument 8 at the surface of the organ 4 and an incision 25 that has been started.

FIG. 8 shows a subsequent frame (e.g., a monitoring image 26 recorded at a later time point). A clear further separation may be identified there, along an incision edge 27 at which the intervention instrument 8 is currently working. Surfaces have formed to the right and left of the incision edge 27, specifically a part-surface 28 of the future resectate to the right and a part-surface 29 of the future remaining tissue surface 7 to the left. The triangles 30 mark the positions of surface features of a correspondence pair already detected in an earlier frame, while the circles 31 in this frame (e.g., in the monitoring image 26) show newly detected surface features of a new correspondence pair, having a relative position to the correspondence features marked by the triangles 30 that may be determined clearly.

FIG. 9 shows a monitoring image 32 at a time point that comes relatively soon after the time point 26. FIG. 9 shows that the intervention instrument 8 is just being moved out of the region of the incision edge 27, suggesting that no action will be performed on the tissue in a subsequent time segment. As a result of the instrument 8 moving away and the previous progress of the resection, further surface features, marked by squares 33 and near to the surface features marked by circles 31, have become visible and form a new correspondence pair.

Returning to FIG. 6, the act S17 concerns the generation or updating of a textured surface map of the resulting surfaces of the resectate 5 and the extraction region 6. Based on the known relative position of the surface features of the correspondence pairs to each other, it is possible initially to create surface models, optionally even in three dimensions using a stereo camera, to which the surface patterns or corresponding image data from at least one of the monitoring images 24, 26, 32 is assigned as texture. The sectors that are used in each case from the monitoring images 24, 26, 32 show at least the corresponding surface feature (e.g., as feature information), though regions between the locations of surface features may also be filled in correspondingly. In this case, the texture may be specified using a plurality of frames (e.g., by averaging over a plurality of monitoring images 24, 26, 32 showing the corresponding portion).

The current correspondence pairs, the textured surface maps for both the future resectate 5 and the extraction region 6, and further information if applicable (e.g., further feature information, relative position, etc.) are stored in a data store of the control entity 17.

In act S18, it is checked whether the end of the relevant section of the monitoring video has been reached. If not, the next frame is processed (e.g., n->n+1). If the end has been reached, the method is terminated.

Provision is also made in act S16 for monitoring whether a one-sided tissue change occurs (e.g., a tissue change affecting only or substantially only the part 28 or the part 29; due to one-sided cauterization by an energy instrument). In such cases, the surface textures of the surface maps are adapted again at the corresponding locations, as is other feature information likewise if necessary. A similarity relationship is thereby produced, for example, in the form of the correspondence pair, which would otherwise not have been identifiable purely based on image-based comparison of the final state.

Figure 5:
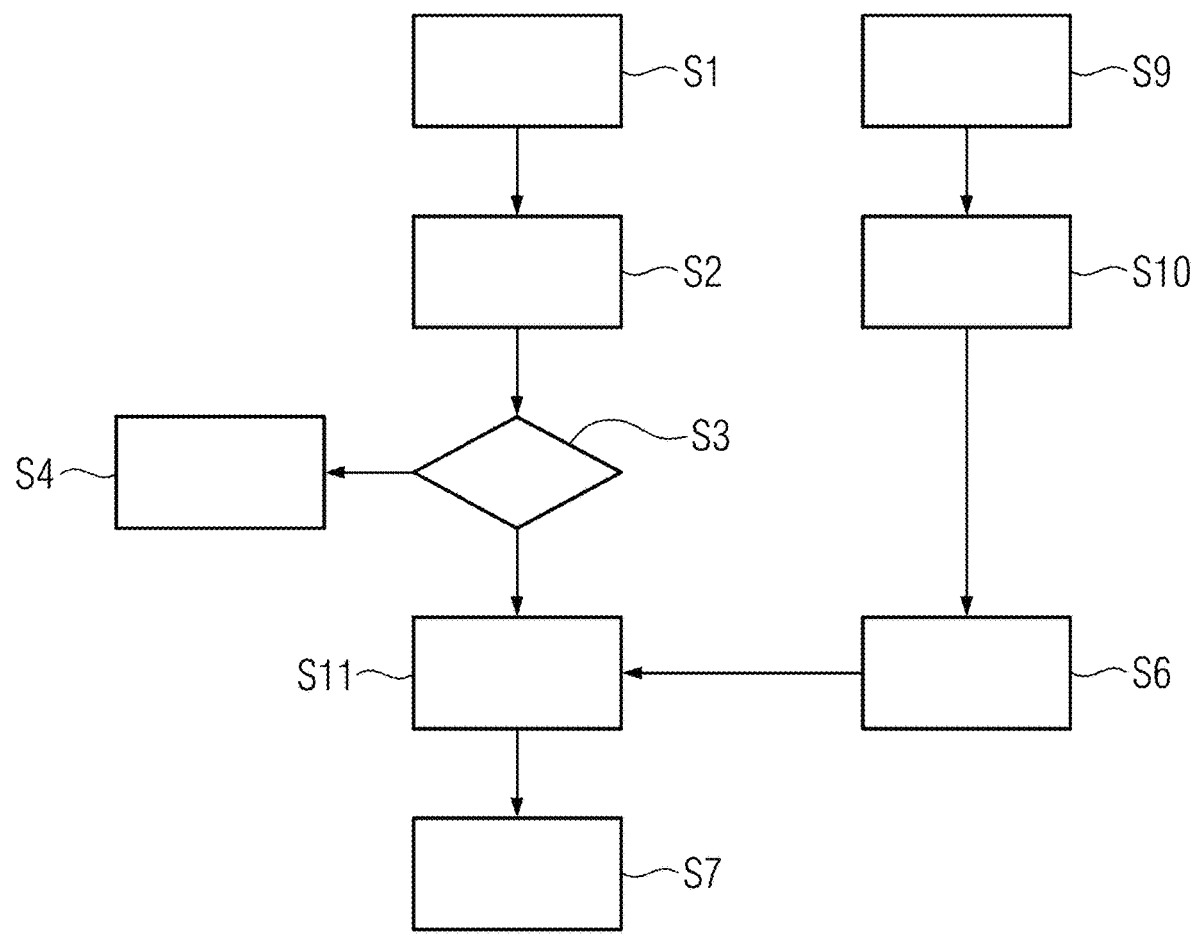
FIG. 5 shows a flow diagram of a third exemplary embodiment of the method.

Accordingly, the correspondence data set may also be used to improve the registration in the acts S6 of the method as per FIG. 3 to FIG. 5, where a further similarity criterion is added based on the correspondence pairs with corresponding feature information (e.g., also fingerprint data sets) and possibly relative positions. Using the similarity criterion, surface features that no longer appear similar due to an excessively thick tissue layer being excavated therebetween or subsequent one-sided processing may nonetheless be identified as corresponding.

Figure 10:
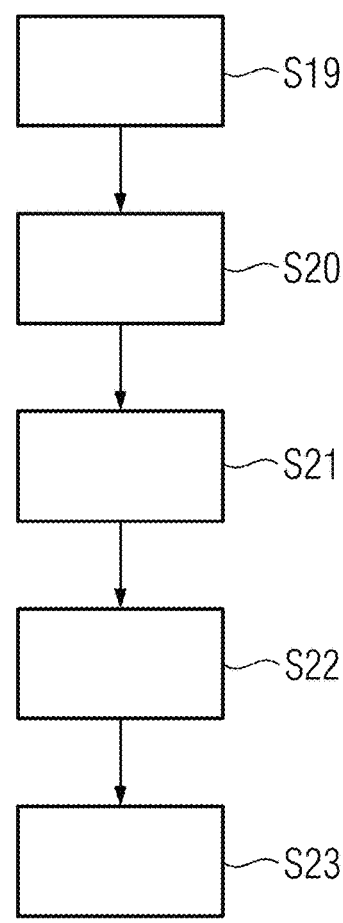
FIG. 10 shows a flow diagram for use of the correspondence data set.

However, an embodiment of the method, as illustrated by the flow diagram in FIG. 10, in which the surface map of the remaining tissue surface 7 of the extraction region 6, which is produced in act S17, ultimately acts as a second surface data set may be provided. If applicable (e.g., if the position of the organ 4 or the patient 3 does not change excessively), this second surface data set is indeed already present in the patient-related coordinate system (e.g., since the remaining tissue surface 7 unlike the resectate 5 is not removed), by which the recording instrument 9, 11 that served to record the monitoring images 24, 26, 32 was also tracked by the navigation system 14. However, further second surface data sets may then be recorded, and, because the further second surface data sets show the same surface, the further second surface data sets may be registered with the surface map of the extraction region 6 in a simple manner in order thereby to establish a relationship to the patient-related coordinate system.

In act S19, from FIG. 10, provision is first made for preprocessing the surface maps of the resectate 5 and the remaining tissue surface 7 in the extraction region 6 as created in act S17. The information relating to the locations of the surface features of the correspondence pairs in the surface maps already represents correspondence information, since these locations are assigned to each other, though this correspondence information is only available at specific points where surface features that were identified as suitable for surface pairs are present. In act S19, these correspondences are then interpolated as appropriate, so that corresponding locations on the remaining tissue surface 7 may be assigned to each location or at least as many locations as possible on the surface of the resectate 5. This ultimately results in a correspondence mapping or correspondence table, which is ideally valid for the complete surface maps and therefore represents a completion of the registration between the surface maps. Since a first surface data set that is recorded using the ex vivo scan appliance 16 may easily be registered with the surface map of the resectate 5 by virtue of the same surface, the association of this registration with the registration that was given by the correspondence information produces a registration between the first surface data set and the surface map of the remaining tissue surface 7 of the extraction region 6, which may be regarded as a second surface data set.

In other words, in act S20, at least that portion of the first surface data set, as recorded using the ex vivo scan appliance 16, which exhibits malignant changes of the tissue near the surface may be registered with the surface map of the resectate 5 in an image-based manner. For example, a microscopy image of the surface of the resectate 5 may be scaled down accordingly, and then spatially assigned to the surface map in an image-based manner. A complete registration of the surface data set with the surface map of the resectate 5 is effected. As a result of the act S20, a location on the surface map of the resectate 5 may therefore be assigned to an indicative feature in every case.

In act S21, the correspondence information is then used to determine the location by corresponding to this location $a_R$.

If the surface map of the extraction region 6 is not already available as a second surface data set in the patient-related coordinate system, an image-based registration may be performed in act S22 between the textures of the surface map of the remaining tissue surface 7, at least around the location by, and a current video image of the laparoscope 12 or another second surface data set. Alternatively, this registration may also be performed by the navigation system 14, where the whole surface map of the remaining tissue surface 7 is registered with the intraoperative geometry, as explained above.

In a similar manner to the acts S7, the performance of support measures may take place in act S23. For example, the surface section of the remaining tissue surface 7 corresponding to the tumor-infiltrated location of the resectate 5 may be displayed as an overlay, augmented reality depiction and/or marking in the navigation system.

Figure 11:
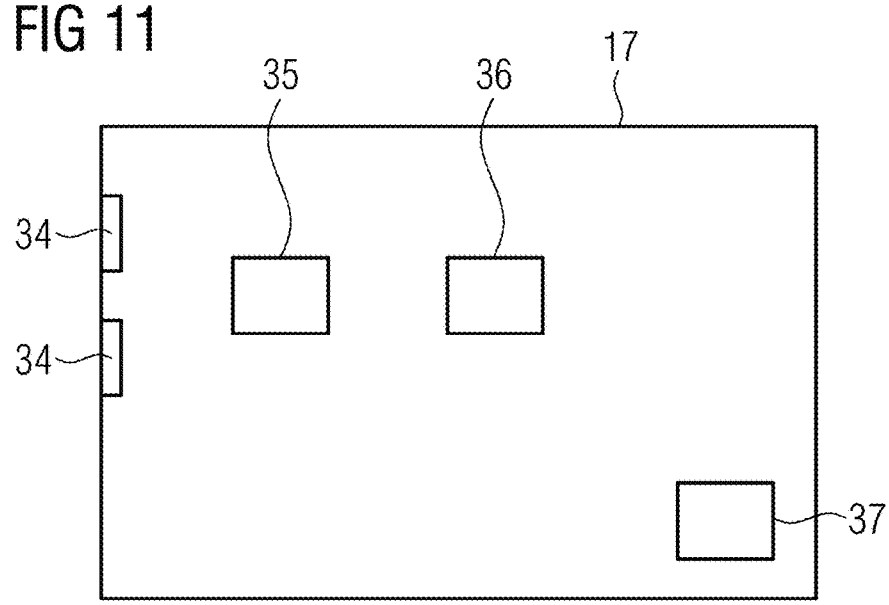
FIG. 11 shows the functional structure of a control entity of an examination system according to an embodiment.

FIG. 11 lastly shows possible functional units of a control entity 17 of a support system 1 according to the present embodiments. The control entity 17 may firstly have interfaces 34, via which the image data required for the relevant exemplary embodiments of the method may be received from the corresponding devices/instruments (e.g., ex vivo scan appliance 16, recording instruments 9, 11, etc.) for processing. The control entity 17 has at least one registration unit 35 for performing the acts S6, S11, S12, S16, S17, S19, S20, S21 and/or S22 according to the exemplary embodiment. A support unit 36 may be provided for performing the acts S7 or S23 according to the exemplary embodiment.

Depending on the specific embodiment of the method, the method is implemented by the control entity 17. Further functional units, possibly including subunits of the registration unit 35 and the support unit 36, may obviously be provided (e.g., at least one image processing unit, at least one preprocessing unit, etc.). A storage device or data store 37 may be used to store intermediate results or the registration result, etc.

Although the invention is illustrated and described in detail with reference to the exemplary embodiments, the invention is not restricted by the examples disclosed herein, and other variations may be derived therefrom by a person skilled in the art without departing from the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for navigational support of a person performing a resection on a patient following extraction of a resectate, for navigation relative to the resectate in an extraction region, the method comprising:
   recording a first surface data set of the resectate using an ex vivo scan appliance;
   determining a second surface data set of the extraction region using a recording instrument, the second surface data set covering at least one part of a remaining tissue surface of the extraction region of the resectate in the patient;
   registering the first surface data set of the resectate with the second surface data set of the extraction region based on corresponding surface features of the resectate and the remaining tissue surface in the extraction region; and
   performing at least one support measure that supports the navigation in the extraction region relative to the resectate, using the registration.

2. The method of claim 1, wherein the recording instrument is tracked in a patient-related coordinate system by a navigation system,
   wherein the second surface data set is also recorded or present in the patient-related coordinate system,
   wherein the at least one support measure comprises a depiction of a position of at least one indicative feature of the resectate relative to the recording instrument, relative to a further instrument that is tracked by the navigation system, in the patient-related coordinate system, relative to a surface of the extraction region, or any combination thereof.

3. The method of claim 2, wherein for the depiction of the relative position, the method further comprises:
   presenting the first surface data set, the second surface data set, or the first surface data set and the second surface data set using an augmented reality appliance, a display appliance, or the augmented reality appliance and the display appliance, wherein the recording instrument, the further instrument, a marking, or any combination thereof displaying the respective relative position is incorporated in the first surface data set, the second surface data set, or the first surface data set and the second surface data set;
   presenting an image currently recorded by the recording instrument the further instrument, another further instrument, or any combination thereof; or
   a combination thereof,
   wherein the at least one indicative feature from the first surface data set is incorporated in the image.

4. The method of claim 2, wherein one or more indicative features of the at least one indicative feature describe a presence of a malignant change in the resectate in a defined proximity to a surface of the resectate, the presence being determined by at least partially automatic evaluation of the first surface data set, a further image data set of the resectate that is registered with the first surface data set, or the first surface data set and the further image data set.

5. The method of claim 4, wherein the first surface data set, the second surface data set, the further image data set, or any combination thereof is recorded using an optical imaging modality, optical coherence tomography, fluorescence imaging, confocal microscopy, laser microscopy, or any combination thereof.

6. The method of claim 4, wherein a digital biopsy tool is used as the recording instrument, the digital biopsy tool being configured to survey the remaining tissue surface in the extraction region in a sector-based manner, and
   wherein the corresponding sector is localized on the surface of the resectate in context of the registration.

7. The method of claim 6, wherein the evaluation of the first surface data set results in at least one region with surface features that are identifiable in surface data of the digital biopsy tool being determined and displayed to a person in relation to the resectate.

8. The method of claim 6, further comprising:
   determining a quality level in the context of the registration, the quality level describing a reliability of a result of the registration; and
   requesting a recording of a further sector when the quality level fails to meet a threshold value, performing at least one verification measurement using the digital biopsy tool such that information given by the at least one support measure is checked, or a combination thereof.

9. The method of claim 8, further comprising performing the at least one verification measurement using the digital biopsy tool, such that presence of a malignant change is checked at a current position of the digital biopsy tool.

10. The method of claim 1, wherein the first surface data set, the second surface data set, or the first surface data set and the second surface data set are assembled from partial data sets recorded from different directions of view relative to the resectate or the extraction region.

11. The method of claim 10, further comprising initially determining a surface model describing a surface contour from the partial data sets, image data of the partial data sets being assigned to the surface model as texture.

12. The method of claim 10, wherein when a second surface data set showing a whole surface of the extraction region formed by the resection is determined, and a digital biopsy tool that surveys the remaining tissue surface in the extraction region (6) in a sector-based manner is used, the method further comprises registering a sector surveyed by the digital biopsy tool on the second surface data set.

13. The method of claim 12, wherein registering the sector surveyed by the digital biopsy tool on the second surface data set comprises registering the sector surveyed by the digital biopsy tool on the second surface data set with aid of the first surface data set, which is registered with the second surface data set.

14. The method of claim 1, wherein:
when using surface data sets that each describe a whole surface, the registration takes place successively at various resolution levels;
a plurality of first surface data sets, a plurality of second surface data sets, or the plurality of first surface data sets and the plurality of second surface data sets are recorded using different modalities, all surface data sets of the plurality of first surface data sets and the plurality of second surface data sets being used for a purpose of registration, the plurality of first surface data sets including the first surface data set and the plurality of second surface data sets including the second surface data set; or
a combination thereof.

15. The method of claim 14, wherein when using surface data sets that each describe a whole surface, the registration takes place successively at various resolution levels, in that superficial tissue structures are segmented as surface features.

16. The method of claim 1, wherein cell structures, cell types, cell arrangements, cell clusters, fiber structures, or any combination thereof of the tissue, vascular structures of the tissue, spectral reflectivities of the tissue, a distribution of a fluorescent dye in the tissue, a distribution of malignant changes on a visible tissue surface, traces of an intervention instrument, or any combination thereof is usable as surface features for a purpose of registration.

17. The method of claim 1, further comprising detecting surface features in different resolution regions of surface data sets are, combining the surface features in the different resolution regions into fingerprint data sets, or a combination thereof using at least one filtering algorithm, smoothing algorithm, edge highlighting algorithm, or any combination thereof; and
comparing the fingerprint data sets for a purpose of registration.

18. The method of claim 16, wherein the first surface data set and the second surface data set are recorded using different modalities when fingerprint data sets are used.

19. The method of claim 1, wherein registering the first surface data set with the second surface data set comprises registering the first surface data set with the second surface data set using an artificial intelligence registration algorithm that has been trained using annotated surface data sets as training data.

20. The method of claim 1, wherein for supporting the registration, the method further comprises generating a correspondence data set including correspondence pairs of reciprocally corresponding surface features, the generating of the correspondence data set comprising:
during the resection of the resectate, continuously recording monitoring images of a current work region using the recording instrument or a further recording instrument;
upon detection of a performance of an incision, detecting surface features of the respective resulting surface on both sides of the incision by automatic evaluation of corresponding monitoring images;
effecting an assignment to each other of surface features that reciprocally correspond in geometric terms relative to the incision, such that a correspondence pair is generated; and
storing each correspondence pair, together with feature information describing the surface features of the correspondence pair in the correspondence data set.

21. The method of claim 20, wherein when generating a new correspondence pair, the method further comprises:
determining a relative position to at least one further correspondence pair already included in the correspondence data set, a relative position to a reference feature that is not part of a correspondence pair, or a combination thereof, the respective determining of the relative position comprising detecting at least one of the surface features of the further correspondence pair, the reference feature in a monitoring image that shows the surface features of the new correspondence pair, or a combination thereof; and
storing the respective relative position in the correspondence data set.

22. The method of claim 21, further comprising creating, based on the correspondence pairs and the respective relative position, surface models of surfaces of the extraction region resulting from the resection and of the resectate are created, at least part of feature information and/or portions of at least one monitoring image showing the corresponding surface region are assigned in a positionally accurate manner in order to determine respective surface maps, such that correspondence information assigning locations on the surface maps to each other is established by means of the correspondence pairs.

23. The method of claim 22, further comprising determining further corresponding locations of the surface maps by interpolation in regions of the surface maps that are situated between the surface features of correspondence pairs, such that the correspondence information provided by the correspondence pairs is expanded.

24. The method of claim 22, wherein the correspondence information is used to localize an indicative feature of the resectate on the remaining tissue surface of the extraction region, the indicative feature having a position that is known on the surface maps of the resectate.

25. The method of claim 20, wherein the detection of the performance of the incision takes place in a manner that is at least partially image-based in the monitoring images, is based on supplementary information that is assigned to the monitoring images relative to time, or a combination thereof.

26. The method of claim 25, wherein the detection of the performance of the incision includes tracking previously detected surface features, an intervention instrument that is visible in the monitoring images, or the previously detected surface features and the intervention instrument that is visible in the monitoring images.

27. The method of claim 25, wherein the supplementary information is determined so as to describe a movement of an intervention instrument, as detected by a navigation system, a supply of energy to the intervention instrument, a workflow step of an intervention workflow, or any combination thereof.

28. The method of claim 20, wherein the surface features of a new correspondence pair are selected such that the surface features of the new correspondence pair are detectable with a reliability that exceeds a threshold value in a respective imaging modality of the surface data sets, at least one further image data set, or the surface data sets and the at least one further image data set.

29. The method of claim 20, wherein the surface features of the correspondence pairs are tracked in the monitoring images over a resection time period for as long as the surface features are contained in the monitoring images, and wherein:
  when a subsequent change of a surface feature by an intervention instrument is detected, the feature information for describing the changed surface feature is adapted;
  when a one-sided change in the surface is detected as a result of automatic evaluation, changed surface features of correspondence data sets are found and associated feature information for describing the changed surface feature is adapted; or
  a combination thereof.

30. A support system for navigational support of a person performing a resection on a patient following extraction of a resectate, for navigation relative to the resectate, the support system comprising:
  a processor configured for navigational support of a person performing a resection on a patient following extraction of a resectate, for navigation relative to the resectate, the processor being configured to:
  record a first surface data set of the resectate using an ex vivo scan appliance;
  determine a second surface data set of the extraction region using a recording instrument, the second surface data set covering at least one part of a remaining tissue surface of the extraction region of the resectate in the patient;
  register the first surface data set of the resectate with the second surface data set of the extraction region based on corresponding surface features of the resectate and the remaining tissue surface in the extraction region; and
  perform at least one support measure that supports the navigation in the extraction region relative to the resectate, using the registration.

31. In a non-transitory computer-readable storage medium that stores instructions executable by one or more processors for navigational support of a person performing a resection on a patient following extraction of a resectate, for navigation relative to the resectate, the instructions comprising:
  recording a first surface data set of the resectate using an ex vivo scan appliance;
  determining a second surface data set of the extraction region using a recording instrument, the second surface data set covering at least one part of a remaining tissue surface of the extraction region of the resectate in the patient;
  registering the first surface data set of the resectate with the second surface data set of the extraction region based on corresponding surface features of the resectate and the remaining tissue surface in the extraction region; and
  performing at least one support measure that supports the navigation in the extraction region relative to the resectate, using the registration.

* * * * *